(12) United States Patent
Landolfi et al.

(10) Patent No.: US 7,223,393 B2
(45) Date of Patent: May 29, 2007

(54) AMPHIREGULIN ANTIBODIES AND THEIR USE TO TREAT CANCER AND PSORIASIS

(75) Inventors: Nicholas F. Landolfi, Menlo Park, CA (US); Naoya Tsurushita, Palo Alto, CA (US); Paul R. Hinton, Sunnyvale, CA (US); Shankar Kumar, Pleasanton, CA (US)

(73) Assignee: PDL Biopharma, Inc, Fremont, CA (US)

( * ) Notice: Subject to any disclaimer, the term of this patent is extended or adjusted under 35 U.S.C. 154(b) by 0 days.

(21) Appl. No.: 10/774,076

(22) Filed: Feb. 6, 2004

(65) Prior Publication Data
US 2004/0210040 A1 Oct. 21, 2004

Related U.S. Application Data

(60) Provisional application No. 60/533,901, filed on Dec. 30, 2003, provisional application No. 60/445,640, filed on Feb. 7, 2003.

(51) Int. Cl.
*A61K 39/395* (2006.01)

(52) U.S. Cl. .............................. 424/133.1; 424/136.1; 424/178.1

(58) Field of Classification Search ............... 424/130, 424/133, 135; 435/335; 530/35
See application file for complete search history.

(56) References Cited

U.S. PATENT DOCUMENTS

| | | | |
|---|---|---|---|
| 4,668,629 A * | 5/1987 | Kaplan et al. ................. | 435/6 |
| 5,115,096 A | 5/1992 | Shoyab et al. | |
| 5,262,298 A | 11/1993 | Shipley et al. | |
| 5,830,995 A | 11/1998 | Shoyab et al. | |
| 5,855,885 A | 1/1999 | Smith et al. | |
| 6,204,359 B1 | 3/2001 | Delaey et al. | |
| 6,677,436 B1 * | 1/2004 | Sato et al. ............... | 530/387.3 |
| 2002/0156263 A1 | 10/2002 | Chen | |

FOREIGN PATENT DOCUMENTS

| | | |
|---|---|---|
| EP | 1 074 617 A2 | 2/2001 |
| EP | 1 249 237 A1 | 10/2002 |
| WO | WO-90/14069 A2 | 11/1990 |
| WO | WO-96/12019 A2 | 4/1996 |
| WO | WO-97/23507 A2 | 7/1997 |
| WO | WO-99/38972 A2 | 8/1999 |
| WO | WO-01/70979 A2 | 9/2001 |
| WO | WO-01/70984 A2 | 9/2001 |
| WO | WO-01/96389 A1 | 12/2001 |
| WO | WO-02/10449 A2 | 2/2002 |
| WO | WO-02/41763 A2 | 5/2002 |
| WO | WO -02/057414 A2 | 7/2002 |
| WO | WO-02/074979 A2 | 9/2002 |
| WO | WO-02/077234 A2 | 10/2002 |
| WO | WO-02/085298 A2 | 10/2002 |
| WO | WO-02/092000 A2 | 11/2002 |
| WO | WO-03/008583 A2 | 1/2003 |
| WO | WO-03/014159 A1 | 2/2003 |
| WO | WO-03/022222 A2 | 3/2003 |

OTHER PUBLICATIONS

Rudikoff et al., Proc Natl Acad Sci., USA 1982, vol. 79, pp. 1979-1983.*
Janeway, immunobiology, 6th Ed. 2004, Garland Sciences, p. 110-112.*
Communication Relating to the Results of the Partial International Search in PCT/US2004/004176.
Cook et al., "A heparin sulfate-regulated human keratinocyte autocrine factor is similar or identical to amphiregulin," Mol. Cell. Biol., 11, 2547-2557 (1991).
Cook et al., "Inhibition of autonomous human keratinocyte proliferation and amphiregulin mitogenic activity by sulfated polysaccharides," In Vitro Cell. Dev. Biol. 28A, 218-222 (1992).
Cook, et al., "Amphiregulin Messenger RNA Is Elevated in Psoriatic Epidermis and Gastrointestinal Carcinomas," Cancer Res. 52: 3224-3227 (1992).
Cook, et al., "Transgenic Expression of the Human Amphiregulin Gene Induces a Psoriasis-like Phenotype," J. Clin. Invest. 100: 2286-2294 (1997).
Damstrup, et al., "Amphiregulin acts as an autocrine growth factor in two human polarizing colon cancer lines that exhibit domain selective EGF receptor mitogenesis," British Journal of Cancer 80(7): 1012-19 (Jun. 1999).
Johnson, G. R., et al., "Amphiregulin induces tyrosine phosphorylation of the epidermal growth factor receptor and p185erbB2. Evidence that amphiregulin acts exclusively through the epidermal growth factor receptor at the surface of human epithelial cells," J. Biol. Chem. 268: 2924-2931 (1993).

(Continued)

*Primary Examiner*—Christina Chan
*Assistant Examiner*—Yunsoo Kim
(74) *Attorney, Agent, or Firm*—Michael Biro; Susan Harlocker

(57) ABSTRACT

The present invention is directed to anti-AR antibodies, preferably humanized monoclonal antibodies having the amino acid sequences disclosed herein. The present invention includes a pharmaceutical composition comprising such antibodies. The present invention includes a method of inhibiting cancer cell growth comprising administering such antibodies into a subject. The present invention also provides a method of treating cancer or psoriasis in a subject in need of such a treatment by administering such antibodies to said subject in a pharmaceutically effective amount.

6 Claims, 23 Drawing Sheets

OTHER PUBLICATIONS

Piepkorn et al., "Amphiregulin-dependent proliferation of cultured human keratinocytes: autocrine growth, the effects of exogenous recombinant cytokine, and apparent requirement for heparin-like glycosaminoglycans," J. Cell. Physiol. 159, 114-120 (1994).

Piepkorn, et al., "Autocrine Regulation of Keratinocytes: the Emerging Role of Heparin-Binding, Epidermal Growth Factor-Related Growth Factors," J. Invest. Dermatol. 111(5):715-721 (Nov. 1998).

Piepkorn, et al., "Overexpression of amphiregulin, a major autocrine growth factor for cultured human keratinocytes, in hyperproliferative skin diseases," Am. J. Dermatol. 18: 165-171 (1996).

Plowman et al., "The amphiregulin gene encodes a novel epidermal growth factor-related protein with tumor-inhibitory activity," Mol. Cell. Biol. 10, 1969-1981 (1990).

Shoyab et al., "Amphiregulin: a bifunctional growth-modulating glycoprotein produced by the phorbol 12-myristate 13-acetate-treated human breast adenocarcinoma cell line MCF-7," Proc. Natl. Acad. Sci. USA 85, 6528-6532 (1988).

Shoyab et al., "Structure and Function of Human Amphiregulin: A Member of the Epidermal Growth Factor Family," Science 243, 1074-1076 (1989).

Thompson, S.A., et al., "COOH-terminal extended recombinant amphiregulin with bioactivity comparable with naturally derived growth factor," J. Biol. Chem. 271(30): 17927-31 (1996).

Cook et al., "Overexpression of Amphiregulin in the Epidermis of Transgenic Mice Induces a Psoriasis-Like Cutaneous Phenotype," J. Invest. Dermatol. 113(5): 860 (Nov. 1999).

\* cited by examiner

Mouse PAR34 mature VH amino acid sequence (SEQ ID NO:2)

```
E I Q L Q Q S G P E L V K P G A S V K V
S C K A S G Y A F T N Y N M Y W V K Q S
H G K S L E W I G Y I D P Y Y G D P G Y
S Q K F K G K A T L T V D K S S S T A Y
M H L N S L T S E D S A V Y Y C A R R G
N F P Y Y F D Y W G Q G T T L T V S S
```

Mouse PAR34 mature VL amino acid sequence (SEQ ID NO:3)

```
D I K M T Q S P S S M Y A S L G E R V T
I T C K A S Q D I N S Y L S W F Q Q K P
G K S P K T L I Y R A N R L V D G V P S
R F S G S G S G Q D Y S L T I S S L E Y
E D M G I Y Y C L Q Y D E F P Y T F G G
G T K L E I K
```

Mouse PAR80 mature VH Region Amino Acid Sequence (SEQ ID NO:4)

```
E V Q L Q Q S G A E L V R S G A S V K L
S C T A S G F N I K D Y Y I H W V K Q R
P E Q G L E W I G C I D P E N G D T E Y
A P N F Q G R A T M T A D T S S N T A Y
L Q L S S L T S E D T A V Y Y C Y G G T
I T F A Y W G Q G T L V T V S A
```

Mouse PAR80 mature VL Region Amino Acid Sequence (SEQ ID NO: 5)

```
Q A V V T Q E S A L T T S P G E T V T L
T C R S S T G A V T T S N S A N W V Q E
K P D H L F T G L I G G T I N R V P G V
P A R F S G S L I G D K A A L T I T G A
Q T E D E A I Y F C A L W Y S N H W V F
G G G T K L T V L G
```

The CDRs based on the definition of Kabat are bolded and underlined.

FIG. 1

Panel of Monoclonal Antibodies Generated Against Human AR

| ANTI-BODY | ISO-TYPE | BINDING | | | | | | | INHIBITION OF AR-EGFR INTER-ACTION | INHIBITION OF AR-MEDIATED PROLIFERATION (μg/ml) | | | | | |
|---|---|---|---|---|---|---|---|---|---|---|---|---|---|---|---|
| | | AR | Surface AR | EGF | HB EGF | Cyno AR | Murine AR | | | 3T3 | | | HEKn | | |
| | | | | | | | | | | IC50% | IC90% | IC50% | IC90% | | |
| PAR2 | IgG1, λ | +++ | +++ | - | - | +++ | +++ | | ++ | 0.13 | 1.3 | 0.35 | >3 | | |
| PAR5 | IgG1, λ | +++ | +++ | - | - | ND | +++ | | ++ | 0.8 | 7.2 | ND | ND | | |
| PAR15 | IgG1, λ | +++ | ++ | - | - | +++ | +++ | | ++ | 0.11 | 0.71 | .2 | >3 | | |
| PAR19 | IgG2b, κ | +++ | +++ | - | - | ND | - | | ++ | 5.9 | >10 | ND | ND | | |
| PAR22 | IgG1, λ | +++ | ++ | - | - | ND | +++ | | ++ | 6.8 | >10 | ND | ND | | |
| PAR23 | IgG1, λ | +++ | ++ | - | - | ND | ++ | | ++ | 1.7 | 6.9 | ND | ND | | |
| PAR26 | IgG2b, κ | +++ | +++ | - | - | ND | - | | ++ | >10 | >10 | >3 | >3 | | |
| PAR29 | IgG1, λ | +++ | +++ | - | - | ND | +++ | | ++ | 0.9 | >10 | ND | ND | | |
| PAR31 | IgG2b, λ | +++ | +++ | - | - | +++ | +++ | | ++ | 0.7 | 1.9 | .07 | >3 | | |
| PAR34 | IgG2b, κ | +++ | ++ | - | - | +++ | +++ | | ++ | 0.072 | 0.71 | .041 | 2.95 | | |
| PAR44 | IgG1, κ | +++ | ++ | - | - | ND | +++ | | ND | 4.1 | >10 | 1.7 | >3 | | |
| PAR46 | IgG1, λ | +++ | ++ | - | - | ND | ++ | | ND | 0.6 | >10 | ND | ND | | |
| PAR51 | IgG1, λ | +++ | ++ | - | - | +++ | - | | ND | 4 | >10 | ND | ND | | |
| PAR67 | IgG2b, κ | +++ | ++ | - | - | ND | - | | ND | >10 | >10 | >3 | >3 | | |
| PAR79 | IgG1, κ | +++ | +++ | - | - | +++ | - | | ND | 2.8 | >10 | ND | ND | | |
| PAR80 | IgG2a, λ | +++ | ++ | - | - | ND | - | | ND | 0.072 | 0.42 | 0.2 | 2.8 | | |
| PAR81 | IgG1, κ | +++ | ++ | - | - | ND | - | | ND | 3.9 | >10 | ND | ND | | |
| PAR84 | IgG2a, λ | +++ | +++ | - | - | +++ | - | | ND | 0.51 | 0.8 | 0.48 | >3 | | |

BINDING – direct binding as detected by ELISA
INHIBITION OF AR-EGFR INTERACTION – ability to inhibit AR binding to A431 (human EGFR+ epidermoid carcinoma)
INHIBITION of PROLIFERATION – inhibition of proliferation of 3T3 (murine) cells to 100 ng exogenous human AR, or HEKn (human) cells to endogenously produced AR
ND – not determined; IC50% is the amount of the antibody needed to accomplish 50% inhibition; IC90% is the amount of the antibody needed to accomplish 90% inhibition

FIG. 2 cDNA (SEQ ID NO:8) and amino acid (SEQ ID NO:9) sequences for the signal peptide and heavy chain variable region of the PAR34 antibody.

```
                              30                              60
ATGGAATGGAGATGGATCTTTCTCTTCCTCCTGTCAGGAACTACAGGTGTCCACTCTGAG
  M   E   W   R   W   I   F   L   F   L   L   S   G   T   T   G   V   H   S   E 90                             120
ATCCAGCTGCAGCAGTCTGGACCTGAGCTGGTGAAGCCTGGGGCTTCAGTGAAGGTATCC
  I   Q   L   Q   Q   S   G   P   E   L   V   K   P   G   A   S   V   K   V   S 150                             180
TGCAAGGCTTCTGGTTATGCATTCACTAACTACAACATGTACTGGGTGAAGCAGAGCCAT
  C   K   A   S   G   Y   A   F   T   N   Y   N   M   Y   W   V   K   Q   S   H 210                             240
GGAAAGAGCCTTGAGTGGATTGGATATATTGATCCTTACTATGGTGATCCTGGCTACAGC
  G   K   S   L   E   W   I   G   Y   I   D   P   Y   Y   G   D   P   G   Y   S 270                             300
CAGAAGTTCAAGGGCAAGGCCACATTGACTGTTGACAAGTCCTCCAGCACAGCCTACATG
  Q   K   F   K   G   K   A   T   L   T   V   D   K   S   S   S   T   A   Y   M 330                             360
CATCTCAACAGCCTGACATCTGAGGACTCTGCAGTCTATTACTGTGCAAGACGGGGTAAC
  H   L   N   S   L   T   S   E   D   S   A   V   Y   Y   C   A   R   R   G   N 390                   414
TTCCCGTACTACTTTGACTACTGGGGCCAAGGCACCACTCTCACAGTCTCCTCA
  F   P   Y   Y   F   D   Y   W   G   Q   G   T   T   L   T   V   S   S
```

FIG. 8 cDNA (SEQ ID NO:10) and amino acid (SEQ ID NO:11) sequences for the signal peptide and light chain variable region of the PAR34 antibody.

```
                                    30                              60
        ATGAGGACCCCTGCTCAGTTTCTTGGAATCTTGTTGCTCTGGTTTCCAGGTATCAAATGT
         M   R   T   P   A   Q   F   L   G   I   L   L   W   F   P   G   I   K   C 90                             120
        GACATCAAGATGACCCAGTCTCCATCTTCCATGTATGCATCTCTAGGAGAGAGAGTCACT
         D   I   K   M   T   Q   S   P   S   S   M   Y   A   S   L   G   E   R   V   T 150                             180
        ATCACTTGCAAGGCGAGTCAGGACATTAATAGCTATTTAAGCTGGTTCCAGCAGAAACCA
         I   T   C   K   A   S   Q   D   I   N   S   Y   L   S   W   F   Q   Q   K   P 210                             240
        GGGAAATCTCCTAAGACCCTGATCTATCGTGCAAACAGATTGGTAGATGGGGTCCCATCA
         G   K   S   P   K   T   L   I   Y   R   A   N   R   L   V   D   G   V   P   S 270                             300
        AGGTTCAGTGGCAGTGGATCTGGGCAAGATTATTCTCTCACCATCAGCAGCCTGGAGTAT
         R   F   S   G   S   G   S   G   Q   D   Y   S   L   T   I   S   S   L   E   Y 330                             360
        GAAGATATGGGAATTTATTATTGTCTACAGTATGATGAGTTTCCGTACACGTTCGGAGGG
         E   D   M   G   I   Y   Y   C   L   Q   Y   D   E   F   P   Y   T   F   G   G

381
        GGGACCAAGCTGGAAATAAAA
         G   T   K   L   E   I   K
```

FIG. 9

Alignment of the VH region amino acid sequences of PAR34 (SEQ ID NO:2), HuPAR34 (SEQ ID NO:12), and the human germline DP-3/JH4 segments (SEQ ID NO:13).

```
                                                                      30
PAR34      E I Q L Q Q S G P E L V K P G A S V K V S C K A S G Y A F T
HuPAR34    E V Q L V Q S G A E V K K P G A S V K I S C K V S G Y A F T
DP-3       E V Q L V Q S G A E V K K P G A T V K I S C K V S G Y T F T

60
PAR34      N Y N M Y W V K Q S H G K S L E W I G Y I D P Y Y G D P G Y
HuPAR34    N Y N M Y W V R Q A P G K G L E W I G Y I D P Y Y G D P G Y
DP-3       - - - - - W V Q Q A P G K G L E W M G - - - - - - - - - - -

90
PAR34      S Q K F K G K A T L T V D K S S S T A Y M H L N S L T S E D
HuPAR34    S Q K F K G K A T L T V D K S T S T A Y M E L S S L R S E D
DP-3       - - - - - - R V T I T A D T S T D T A Y M E L S S L R S E D

119
PAR34      S A V Y Y C A R R G N F P Y Y F D Y W G Q G T T L T V S S
HuPAR34    T A V Y Y C A R R G N F P Y Y F D Y W G Q G T L V T V S S
DP-3/JH4   T A V Y Y C A T - - - - - - - - - - W G Q G T L V T V S S
```

FIG. 10

Alignment of the VL region amino acid sequences of PAR34 (SEQ ID NO:3), HuPAR34 (SEQ ID NO:14), and the human germline L1 and JK4 segments (SEQ ID NO:15).

```
                                                            30
PAR34     D I K M T Q S P S S M Y A S L G E R V T I T C K A S Q D I N
HuPAR34   D I Q M T Q S P S S L S A S V G D R V T I T C K A S Q D I N
L1        D I Q M T Q S P S S L S A S V G D R V T I T C - - - - - - -

60
PAR34     S Y L S W F Q Q K P G K S P K T L I Y R A N R L V D G V P S
HuPAR34   S Y L S W F Q Q K P G K A P K T L I Y R A N R L V D G V P S
L1        - - - - W F Q Q K P G K A P K S L I Y - - - - - - - G V P S

90
PAR34     R F S G S G S G Q D Y S L T I S S L E Y E D M G I Y Y C L Q
HuPAR34   R F S G S G S G Q D Y T L T I S S L Q P E D F A T Y Y C L Q
L1        R F S G S G S G T D F T L T I S S L Q P E D F A T Y Y C - -

107
PAR34     Y D E F P Y T F G G G T K L E I K
HuPAR34   Y D E F P Y T F G G G T K V E I K
Jk4       - - - - - - - F G G G T K V E I K
```

FIG. 11

Nucleotide sequence (SEQ ID NO:16) and deduced amino acid sequence (SEQ ID NO:17) of the heavy chain variable region (including the signal peptide sequence) of HuPAR34 in the mini exon.

```
                            30                                        60
       ACGCGTCCACCATGGAATGGAGATGGATCTTTCTCTTCCTCCTGTCAGGAACTACAGGTG
                    M   E   W   R   W   I   F   L   F   L   L   S   G   T   T   G 90                                       120
       TCCACTCTGAGGTCCAGCTGGTGCAGTCTGGAGCTGAGGTGAAGAAGCCTGGGGCTTCTG
        V   H   S   E   V   Q   L   V   Q   S   G   A   E   V   K   K   P   G   A   S 150                                       180
       TGAAAATATCCTGCAAGGTTTCTGGTTATGCATTCACTAACTACAACATGTATTGGGTGA
        V   K   I   S   C   K   V   S   G   Y   A   F   T   N   Y   N   M   Y   W   V 210                                       240
       GGCAGGCCCCTGGAAAGGGCCTTGAGTGGATTGGATATATTGATCCTTACTATGGTGATC
        R   Q   A   P   G   K   G   L   E   W   I   G   Y   I   D   P   Y   Y   G   D 270                                       300
       CTGGCTACAGCCAGAAGTTCAAGGGCAAGGCCACATTGACTGTTGACAAGTCCACCAGCA
        P   G   Y   S   Q   K   F   K   G   K   A   T   L   T   V   D   K   S   T   S 330                                       360
       CAGCCTACATGGAGCTCAGCAGCCTGAGGTCTGAGGACACTGCAGTCTATTACTGTGCAA
        T   A   Y   M   E   L   S   S   L   R   S   E   D   T   A   V   Y   Y   C   A 390                                       420
       GACGTGGCAACTTCCCGTACTACTTTGACTACTGGGGCCAAGGCACCCTTGTCACAGTCT
        R   R   G   N   F   P   Y   Y   F   D   Y   W   G   Q   G   T   L   V   T   V

448
       CATCAGGTGAGTCCTCACAACCTCTAGA
        S   S
```

FIG. 12

Nucleotide sequence (SEQ ID NO:18) and deduced amino acid sequence (SEQ ID NO:19) of the light chain variable region (including the signal peptide sequence) of HuPAR34 in the mini exon.

```
                           30                                  60
ACGCGTCCACCATGAGGACCCCTGCTCAGTTTCTTGGTATCTTGTTGCTCTGGTTTCCTG
              M   R   T   P   A   Q   F   L   G   I   L   L   W   F   P 90                                 120
GTATCAAATGTGACATCCAGATGACCCAGTCTCCATCTTCCCTGTCTGCATCTGTTGGAG
 G   I   K   C   D   I   Q   M   T   Q   S   P   S   S   L   S   A   S   V   G 150                                 180
ACAGGGTCACTATCACTTGCAAAGCAAGTCAGGACATTAATAGCTATTTAAGCTGGTTCC
 D   R   V   T   I   T   C   K   A   S   Q   D   I   N   S   Y   L   S   W   F 210                                 240
AGCAGAAACCAGGGAAAGCTCCTAAGACCCTGATCTATCGTGCAAACAGATTGGTAGATG
 Q   Q   K   P   G   K   A   P   K   T   L   I   Y   R   A   N   R   L   V   D 270                                 300
GGGTCCCATCAAGATTCAGTGGCAGTGGATCTGGGCAAGATTATACTCTCACCATCAGTA
 G   V   P   S   R   F   S   G   S   G   S   G   Q   D   Y   T   L   T   I   S 330                                 360
GCCTGCAGCCTGAGGATTTCGCAACTTATTATTGTCTACAGTATGATGAGTTTCCGTACA
 S   L   Q   P   E   D   F   A   T   Y   Y   C   L   Q   Y   D   E   F   P   Y 390                   415
CGTTCGGAGGAGGGACCAAGGTGGAAATAAAACGTAAGTGCACTTTCCTTCTAGA
 T   F   G   G   G   T   K   V   E   I   K
```

FIG. 13

Oligonucleotide primers used for the synthesis of the HuPAR34 VH gene.

Oligonucleotide 1 (SEQ ID NO:20)
5'-CTAGCCACGCGTCCACCATGGAATGGAGATGGATCTTTCTCTTCCTCCTGTCAGGAACTACAGGTGTCCACTCTG-3'

Oligonucleotide 2 (SEQ ID NO:21)
5'-TTCACAGAAGCCCCAGGCTTCTTCACCTCAGCTCCAGACTGCACCAGCTGGACCTCAGAGTGGACACCTGTAGTTCC-3'

Oligonucleotide 3 (SEQ ID NO:22)
5'-AAGCCTGGGGCTTCTGTGAAAATATCCTGCAAGGTTTCTGGTTATGCATTCACTAACTACAACATGTATTGGGTG-3'

Oligonucleotide 4 (SEQ ID NO:23)
5'-CCATAGTAAGGATCAATATATCCAATCCACTCAAGGCCCTTTCCAGGGGCCTGCCTCACCCAATACATGTTGTAGTTAG-3'

Oligonucleotide 5 (SEQ ID NO:24)
5'-GGATATATTGATCCTTACTATGGTGATCCTGGCTACAGCCAGAAGTTCAAGGGCAAGGCCACATTGAC-3'

Oligonucleotide 6 (SEQ ID NO:25)
5'-TGTCCTCAGACCTCAGGCTGCTGAGCTCCATGTAGGCTGTGCTGGTGGACTTGTCAACAGTCAATGTGGCCTTGCCCTTG-3'

Oligonucleotide 7 (SEQ ID NO:26)
5'-GCAGCCTGAGGTCTGAGGACACTGCAGTCTATTACTGTGCAAGACGTGGCAACTTCCCGTACTACTTTGACTACTGGGG-3'

Oligonucleotide 8 (SEQ ID NO:27)
5'-GACTCGTCTAGAGGTTGTGAGGACTCACCTGATGAGACTGTGACAAGGGTGCCTTGGCCCCAGTAGTCAAAGTAGTACG-3'

Oligonucleotide 9 (SEQ ID NO:28)
5'-CTAGCCACGCGTCCACCATG-3'

Oligonucleotide 10 (SEQ ID NO:29)
5'-GACTCGTCTAGAGGTTGTGAG-3'

FIG. 15

Oligonucleotide primers used for the synthesis of the HuPAR34 VL gene.

Oligonucleotide 1 (SEQ ID NO:30)
5'-CTAGCCACGCGTCCACCATGAGGACCCCTGCTCAGTTTCTTGGTATCTTGTTGCTCTGGTTTCCTGGTATC-3'

Oligonucleotide 2 (SEQ ID NO:31)
5'-CAACAGATGCAGACAGGGAAGATGGAGACTGGGTCATCTGGATGTCACATTTGATACCAGGAAACCAGAGCAAC-3'

Oligonucleotide 3 (SEQ ID NO:32)
5'-CTTCCCTGTCTGCATCTGTTGGAGACAGGGTCACTATCACTTGCAAAGCAAGTCAGGACATTAATAGC-3'

Oligonucleotide 4 (SEQ ID NO:33)
5'-GATCAGGGTCTTAGGAGCTTTCCCTGGTTTCTGCTGGAACCAGCTTAAATAGCTATTAATGTCCTGACTTGC-3'

Oligonucleotide 5 (SEQ ID NO:34)
5'-GAAAGCTCCTAAGACCCTGATCTATCGTGCAAACAGATTGGTAGATGGGGTCCCATCAAGATTCAGTGGCAGTGGATC-3'

Oligonucleotide 6 (SEQ ID NO:35)
5'-CCTCAGGCTGCAGGCTACTGATGGTGAGAGTATAATCTTGCCCAGATCCACTGCCACTGAATCTTG-3'

Oligonucleotide 7 (SEQ ID NO:36)
5'-CAGTAGCCTGCAGCCTGAGGATTTCGCAACTTATTATTGTCTACAGTATGATGAGTTTCCGTACACGTTCGGAGG-3'

Oligonucleotide 8 (SEQ ID NO:37)
5'-GACTCGTCTAGAAGGAAAGTGCACTTACGTTTTATTTCCACCTTGGTCCCTCCTCCGAACGTGTACGGAAAC-3'

Oligonucleotide 9 (SEQ ID NO:38)
5'-CTAGCCACGCGTCCACCATG-3'

Oligonucleotide 10 (SEQ ID NO:39)
5'-GACTCGTCTAGAAGGAAAG-3'

FIG. 16

Control: KBM
Ab A: Control Antibody
Ab B: anti-amphiregulin antibody

Cell Counts - Fibroblasts
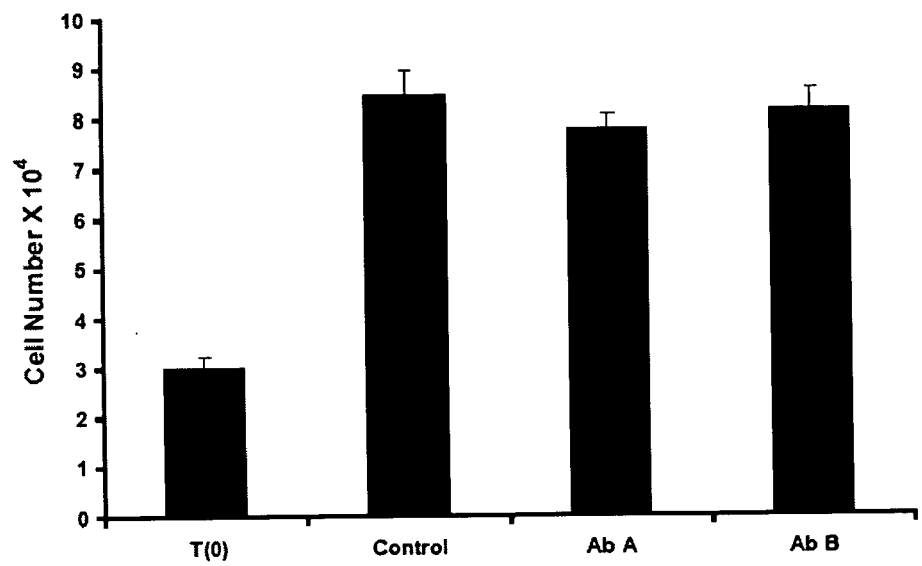
Procollagen production - Fibroblasts
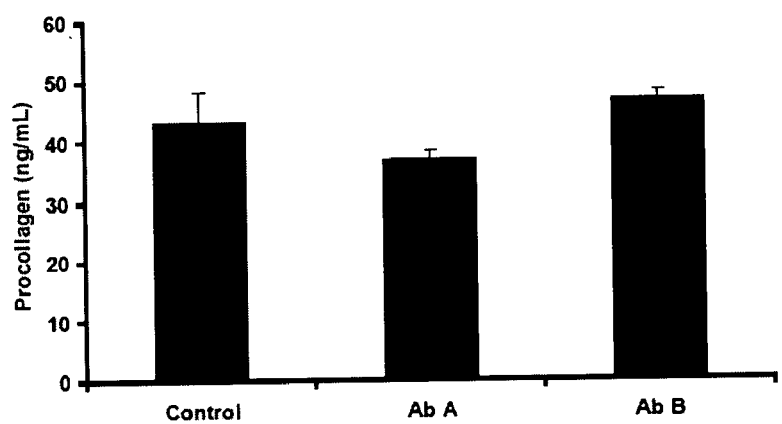
Control: KBM
Ab A: Control Antibody
Ab B: anti-amphiregulin antibody
FIG. 23

AMPHIREGULIN ANTIBODIES AND THEIR USE TO TREAT CANCER AND PSORIASIS

REFERENCE TO RELATED APPLICATIONS

This application claims priority from U.S. provisional patent application Nos. 60/533,901, filed Dec. 30, 2003, and 60/445,640, filed Feb. 7, 2003, each of which is hereby incorporated by reference herein in its entirety.

FIELD OF THE INVENTION

The present invention relates to the field of immunology. In particular, it concerns antagonists of amphiregulin (AR), preferably anti-AR antibodies, and the detection or treatment of cancer or psoriasis by using such antagonists.

BACKGROUND OF THE INVENTION

Amphiregulin is a heparin-binding glycoprotein of approximately 20 kDa which was originally purified from phorbol ester-treated MCF-7 human breast carcinoma cells. The factor belongs to the EGF-family of growth factors and stimulates the proliferation of several cell types (including keratinocytes and some fibroblast cell lines), while inhibiting the proliferation of other cells (including many carcinoma cell lines) (Shoyab et al., Proc. Natl. Acad. Sci. USA 85, 6528–6532 (1988); Shoyab et al., Science 243, 1074–1076 (1989)). Studies have revealed that AR is a major keratinocyte autocrine factor (Cook et al., Mol. Cell. Biol., 11, 2547–2557 (1991); Cook et al., In Vitro Cell. Dev. Biol. 28A, 218–222 (1992); Piepkorn et al., J. Cell. Physiol. 159, 114–120 (1994)). A special feature of AR is that its biological activity is completely blocked in the presence of heparin sulphate. AR has been reported to be the only growth factor displaying this property (Cook et al., Mol. Cell. Biol., 11, 2547–2557 (1991); Cook et al., In Vitro Cell. Dev. Biol. 28A, 218–222 (1992), Piepkorn et al., J. Cell. Physiol. 159, 114–120 (1994)). An isolated AR is disclosed in U.S. Pat. No. 5,115,096 (This and all other U.S. patents and patent applications cited herein are hereby incorporated by reference in their entirety).

Multiple soluble active isoforms of AR are produced by the proteolytic cleavage of a membrane-anchored AR precursor. These active isoforms are AR78, AR81, AR84, AR87, AR92, and AR98, etc. (Shoyab et al, Science 243, 1074–1076 (1989), Plowman et al., Mol. Cell. Biol. 10, 1969–1981 (1990); Thompson, S. A., et al., J. Biol. Chem. 271(30): 17927–31 (1996)). Soluble, secreted AR exerts its tyrosine phosphorylation and mitogenic affects largely through binding and activation of the 170 kDa EGFR (Johnson, G. R., et al., J. Biol. Chem. 268: 2924–2931 (1993)).

Immunolabeling and northern analyses have indicated that AR is low to undetectable in normal adult epidermis and markedly over-expressed in some neoplastic and non-neoplastic hyperproliferative disorders of the epidermis, including appendageal tumors, actinic keratoses, verrucae, and sequamous cell carcimomas (Piepkorn, et al., Am. J. Dermatol. 18: 165–171 (1996)). Studies have demonstrated that AR acts as an autocrine growth factor in human colon cancer. Basolateral administration of neutralizing antibodies against AR reduces the basal DNA replication of colon cancer cells (Damstrup, L. et al., Br. J. Cancer 80(7): 1012–9 (1999)).

It has been reported that mRNA expression of AR is dramatically elevated in psoriatic skin (Cook, et al., Cancer Res. 52: 3224–3227 (1992)). There is also strong AR staining in the cytoplasm of keratinocytes with psoriatic epidermis, in contrast to the sparse, focal labeling restricted to keratinocyte nuclei in normal skin. Keratinocyte-specific transgenic expression results in lesions with striking histological similarity to human psoriasis (Cook, et al., J. Clin. Invest. 100: 2286–2294 (1997)).

Published patent application EP 1249237A1 discloses an AR expression inhibitor and the use thereof as an ameliorating agent for aged skin.

International patent application WO 90/14069 and U.S. Pat. No. 5,262,298 disclose the isolation of keratineocyte autocrine factor (KAF) having the matched amino acid sequence of AR. These two references generally discuss that administration of an inhibitor of KAF activity would benefit conditions such as psoriasis as well as squamous cell carcinomas.

U.S. Pat. No. 5,830,995 and U.S. Pat. No. 6,204,359 disclosed antibodies against AR.

The present invention is directed to neutralizing anti-AR antibodies having the disclosed amino acid sequences or binding characteristics, which are not disclosed in the above-referenced publications. The in vivo efficacy of the anti-AR antibodies for treating psoriasis and cancer are tested in the present invention. These antibodies will find use for inhibiting cancer cell growth, wound healing, enhancing skin quality, or/and treating psoriasis in a subject. The present invention is also pursuant to methods of treating psoriasis or epidermal and pancreatic cancers with any antagonists of AR, preferably, anti-AR antibodies, and more preferably, the antibodies claimed herein.

SUMMARY OF THE INVENTION

The present invention provides anti-AR antibodies that are useful for therapeutic purposes. For example, the antibodies of the present invention may be used therapeutically to treat patients suspected of having or those having been diagnosed with cancer and/or other proliferative conditions, including benign proliferative conditions. In a preferred embodiment, the anti-AR antibodies of the present invention may be used to treat patients diagnosed with psoriasis. In an alternative embodiment, the anti-AR antibodies of the invention may be conjugated with cytotoxic agents and used against AR expressing tumor cells. In one aspect, the AR antibodies of the present invention may be used to treat any proliferative disorder associated with AR expressing cells.

The present invention provides high affinity antibodies for an AR protein (e.g. SEQ ID NO:1). In one embodiment, the present invention provides an antibody that competitively inhibits binding of AR polypeptide to a AR antibody selected from the group consisting PAR34, PAR80, and HuPAR34. Other selected antibodies that may be useful in this embodiment are disclosed in FIG. 2.

In other embodiments, the invention provides an antibody conjugated to an effector moiety or component. The effector moiety may be a label (e.g., a fluorescent label, an effector domain, e.g. MicA) or can be a cytotoxic agent (e.g., a radioisotope or a cytotoxic chemical). In one preferred embodiment, the antibody of the present invention cytotoxic agent auristatin. In other embodiments the antibodies may be used alone to inhibit tumor cell growth. In another preferred embodiment of the invention, the antibody mediates antibody dependent cellular toxicity.

The anti-AR antibodies provided by the present invention include chimeric, humanized and human antibodies. In some embodiments, the invention provides primatized anti-AR antibodies for treatment of primate patients. The present invention provides anti-AR antibodies that are whole antibodies, as well as anti-AR antibody fragments. In preferred embodiments the antibody fragments include Fab, Fab', F(ab')$_2$, Fv fragments, rIgG, diabodies, single chain antibodies, and multispecific antibodies.

Anti-AR antibodies of the present invention include antibodies with 95% or greater homology to the nucleotide and amino acid sequences of the $V_H$ and $V_L$ regions disclosed as SEQ ID NOs: 2–5, 8–12, 14–19). In one preferred embodiment, the invention provides an anti-AR antibody comprising a $V_H$ region amino acid sequence selected from SEQ ID NOs:2, 4, and 12, and/or a $V_L$ region amino acid sequence selected from SEQ ID NOs:3, 5, and 14. In one embodiment, the invention provides an antibody comprising SEQ ID NO:2 and/or SEQ ID NO:3, which correspond to the $V_H$ and $V_L$ regions of PAR34, respectively. In another embodiment, the invention provides an antibody comprising SEQ ID NO:4 and/or SEQ ID NO:5, which correspond to the $V_H$ and $V_L$ regions of PAR80, respectively. In another embodiment, the invention provides an antibody comprising SEQ ID NO:12 and/or SEQ ID NO:14, which correspond to the $V_H$ and $V_L$ regions of HuPAR34, respectively.

In another embodiment, the present invention provides an antibody comprising a mature heavy chain variable region ($V_H$) having an amino acid sequence selected from SEQ ID NOs:2, 4, and 12 and/or a mature light chain variable region ($V_L$) having an amino acid sequence selected from SEQ ID NOs:3, 5 and 14.

The present invention also provides a monoclonal antibody (or antibody fragment thereof) that binds a polypeptide that comprises a sequence at least 80% homologous (and preferably 98% homologous) to the amino acid sequence of the AR protein (SEQ ID NO:1). In some embodiments, the AR monoclonal antibody of the invention is chimeric, humanized or human. Preferably, the monoclonal antibody competes for a ligand binding site on AR, and more preferably it inhibits proliferation of epithelial cells or tumor cells in vivo, wherein the cells are AR-expressing tumor cells. In some embodiments, the monoclonal antibody is conjugated to an effector moiety, such as a cytotoxic agent (e.g. auristatin). In an additional embodiment, the invention provides a monoclonal antibody that mediates antibody dependent cellular cytotoxicity.

In another embodiment, the invention provides monoclonal antibody that binds to the same AR epitope as that bound by an anti-AR antibody selected from group consisting of PAR34, PAR80 and HuPAR34.

In another embodiment, the invention provides an isolated polynucleotide encoding an amino acid sequence selected from the group consisting of SEQ ID NOs:2–5, 12 and 14.

In another embodiment, the invention provides an isolated polynucleotide comprising a nucleic acid sequence selected from the group consisting of SEQ ID NOs:8 ,10, 16 and 18.

In another embodiment, the invention provides a vector comprising a nucleic acid sequence selected from the group consisting of SEQ ID NOs:8, 10, 16 and 18.

In another embodiment, the invention provides a host cell capable of producing an anti-AR antibody selected from group consisting of PAR34, PAR80 and HuPAR34. In some embodiments, the host cell is a hybridoma. In some embodiments the host cell comprises a nucleic acid sequence selected from the group consisting of SEQ ID NOs:8, 10, 16 and 18. In preferred embodiments, the host cell is selected from the group consisting of a Chinese Hamster Ovary (CHO) cell, E. coli, yeast cell, and insect cell.

The invention also provides pharmaceutical compositions comprising a pharmaceutically acceptable excipient and an AR antagonist. In one embodiment, the invention provides a composition comprising an anti-AR antibody and a pharmaceutically acceptable carrier or excipient. In one preferred embodiment, the pharmaceutical composition comprises an anti-AR antibody comprising a mature heavy chain variable region ($V_H$) having an amino acid sequence selected from SEQ ID NOs:2, 4, and 12 and/or a mature light chain variable region ($V_L$) having an amino acid sequence selected from SEQ ID NOs:3, 5 and 14. In another preferred embodiment, the anti-AR antibody is a selected from group consisting of PAR34, PAR80 and HuPAR34.

In some embodiments of the pharmaceutical composition, the anti-AR antibody is conjugated to an effector moiety or component. The effector component may be a label (e.g., a fluorescent label) or can be cytotoxic agent (e.g., a radioisotope or a cytotoxic chemical moiety). The invention provides a variety of cytoxic agents that may be conjugated to an anti-AR antibody including: diphtheria A chain, exotoxin A chain, ricin A chain, abrin A chain, curcin, crotin, phenomycin, neomycin and auristatin. The anti-AR antibodies in the pharmaceutical compositions may be whole antibodies or may be antibody fragments (e.g. include Fab, Fab', F(ab')$_2$, Fv fragments, rIgG, diabodies, single chain antibodies, and multispecific antibodies). In some embodiments, the pharmaceutical composition includes a chimeric, humanized, or human anti-AR antibody.

The invention also provides methods of inhibiting proliferation of a cancer-associated cell. The method comprises contacting the cell with an anti-AR antibody of the invention. In preferred embodiments, the anti-AR antibody capable of binding to an amino acid sequence having at least 80% homology to an AR amino acid sequence (e.g. SEQ ID NO:1). In some embodiments, the anti-AR antibody may be conjugated with an effector moiety (e.g. a cytotoxic agent). In most embodiments, the cancer-associated cell is in a patient, typically a human. In some embodiments, the patient may be diagnosed with and undergoing a therapeutic regimen to treat a metastatic cancer, or may simply be suspected of having cancer.

In another embodiment, the present invention provides a method of treating cancer in a subject in need of such a treatment by administering to said subject a pharmaceutically effective amount of anti-AR antibodies comprising a mature heavy chain variable region ($V_H$) having an amino acid sequence selected from SEQ ID NOs:2, 4, and 12 and/or a mature light chain variable region ($V_L$) having an amino acid sequence selected from SEQ ID NOs:3, 5 and 14.

In alternative embodiments, the methods of treatment of the present invention comprise administering an anti-AR antibody and a therapeutically effective amount of a cytotoxic agent to a patient wherein the antibodies and cytotoxic agent may administered simultaneously, or either one before the other. In another alternative, the cytotoxic agent is conjugated to the antibody and thereby added simultaneously.

In another embodiment, the present invention provides a method of treating psoriasis in a subject in need of such a treatment comprising administering to said subject a therapeutically effective amount of an antagonist of AR. In one preferred embodiment the antagonist administered is an anti-AR antibody capable of binding to an amino acid sequence having at least 80% homology to an AR amino acid sequence (e.g. SEQ ID NO:1). More preferably, the antagonist is an anti-AR antibody comprising a mature heavy chain variable region ($V_H$) having an amino acid sequence selected from SEQ ID NOs:2, 4, and 12 and/or a mature light chain variable region ($V_L$) having an amino acid sequence selected from SEQ ID NOs:3, 5 and 14. In a particularly preferred embodiment, the AR antagonist is selected from group consisting of PAR34, PAR80 and HuPAR34.

The invention further provides diagnostic tests and immunoassays employing the various anti-AR antibodies disclosed herein. In preferred embodiments, these methods involve detecting psoriasis or a cancer cell in a biological sample from a patient by contacting the biological sample with an anti-AR antibody of the invention. In some embodiments, the antibody is conjugated to a label such as fluorescent label or radioisotope.

In one preferred embodiment, the invention provides a method of diagnosing psoriasis or a cancer in a mammal, comprising: contacting an anti-AR antibody with a test sample obtained from the mammal; and detecting the formation of a complex between the antibody and a polypeptide of the test sample; wherein the antibody binds the polypeptide comprising an amino acid sequence having at least 80% homology to the amino acid sequence of an AR (e.g. SEQ ID NO:1). In preferred embodiments of this method, the test sample is obtained from an individual suspected of having neoplastic cell growth or proliferation, or from an individual suspected of having cancer or psoriasis.

BRIEF DESCRIPTION OF THE DRAWINGS

FIG. 1 depicts the amino acid sequences of the mature heavy chain variable region (VH) (SEQ ID NO:2) and mature light chain variable region (VL) (SEQ ID NO:3) of anti-AR antibody, PAR34; and the amino acid sequences of mature heavy chain variable region (VH) (SEQ ID NO:4) and mature light chain variable region (VL) (SEQ ID NO:5) of anti-AR antibody, PAR80.

FIG. 2 depicts the panel of positive monoclonal antibodies generated against human AR. The depicted data includes the antibody isotypes, binding characteristics, and neutralizing capability.

FIG. 8 depicts the cDNA sequence (SEQ ID NO:8) for the heavy chain variable region of the PAR34 antibody. The deduced amino acid sequence (SEQ ID NO:9) is shown below the nucleotide sequence. The signal peptide sequence is in italics. The CDRs based on the definition of Kabat et al. (Sequences of Proteins of Immunological Interest, 5th ed., National Institutes of Health, Bethesda, Md. (1991)) are underlined. The mature heavy chain begins with a glutamic acid (E) residue (bold and double-underlined).

FIG. 9 depicts the cDNA sequence (SEQ ID NO:10) for the light chain variable region of the PAR34 antibody. The deduced amino acid sequence (SEQ ID NO:11) is shown below the nucleotide sequence. The signal peptide sequence is in italics. The CDRs based on the definition of Kabat et al. (Sequences of Proteins of Immunological Interest, 5th ed., National Institutes of Health, Bethesda, Md. (1991)) are underlined. The mature light chain begins with an aspartic acid (D) residue (bold and double-underlined).

FIG. 10 depicts the alignment of the VH region amino acid sequences of PAR34 (SEQ ID NO:2) and HuPAR34 (SEQ ID NO:12), and the human germline DP-3 and JH4 segments (SEQ ID NO:13), shown in single letter code. The CDR sequences based on the definition of Kabat (Sequences of Proteins of Immunological Interest, 5th ed., National Institutes of Health, Bethesda, Md. (1991)) are underlined in the PAR34 VH sequence. The CDR sequences in the human VH segment are omitted in the figure. The single underlined amino acids in the HuPAR34 VH sequence were predicted to contact the CDR sequences and therefore substituted with the corresponding mouse residues. The double underlined amino acids were substituted with consensus human residues to reduce potential immunogenicity.

FIG. 11 depicts the alignment of the VL region amino acid sequences of PAR34 (SEQ ID NO:3), HuPAR34 (SEQ ID NO:14), and the human germline L1 and JK4 segments (SEQ ID NO:15), shown in single letter code. The CDR sequences based on the definition of Kabat (Sequences of Proteins of Immunological Interest, 5th ed., National Institutes of Health, Bethesda, Md. (1991)) are underlined in the PAR34 VL sequence. The CDR sequences in the human VL segment are omitted in the figure. The single underlined amino acids in the HuPAR34 VL sequence were predicted to contact the CDR sequences and therefore substituted with the corresponding mouse residue.

FIG. 12 depicts the nucleotide sequence (SEQ ID NO:16) and deduced amino acid sequence (SEQ ID NO:17) of the heavy chain variable region of HuPAR34 in the mini exon. The signal peptide sequence is in italics. The CDRs based on the definition of Kabat et al. (Sequences of Proteins of Immunological Interest, 5th ed., National Institutes of Health, Bethesda, Md. (1991)) are underlined. The mature heavy chain begins with a glutamic acid (E) residue (bold and double-underlined). The sequence shown is flanked by unique MluI (ACGCGT) and XbaI (TCTAGA) sites.

FIG. 13 depicts the nucleotide sequence (SEQ ID NO:18) and deduced amino acid sequence (SEQ ID NO:19) of the light chain variable region of HuPAR34 in the mini exon. The signal peptide sequence is in italics. The CDRs based on the definition of Kabat et al. (Sequences of Proteins of Immunological Interest, 5th ed., National Institutes of Health, Bethesda, Md. (1991)) are underlined. The mature light chain begins with an aspartic acid (D) residue (bold and double-underlined). The sequence is flanked by unique MluI (ACGCGT) and XbaI (TCTAGA) sites.

FIG. 15 depicts the oligonucleotide primers (SEQ ID NOs:20–29) used for the synthesis of the HuPAR34 VH gene.

FIG. 16 depicts the oligonucleotide primers (SEQ ID NOs:30–39) used for the synthesis of the HuPAR34 VL gene.

FIG. 23 depicts results of in vitro assays of the effect of HuPAR34 or Ig2b on dermal fibroblasts in monolayer culture.

DETAILED DESCRIPTION OF THE INVENTION

Figure 3:
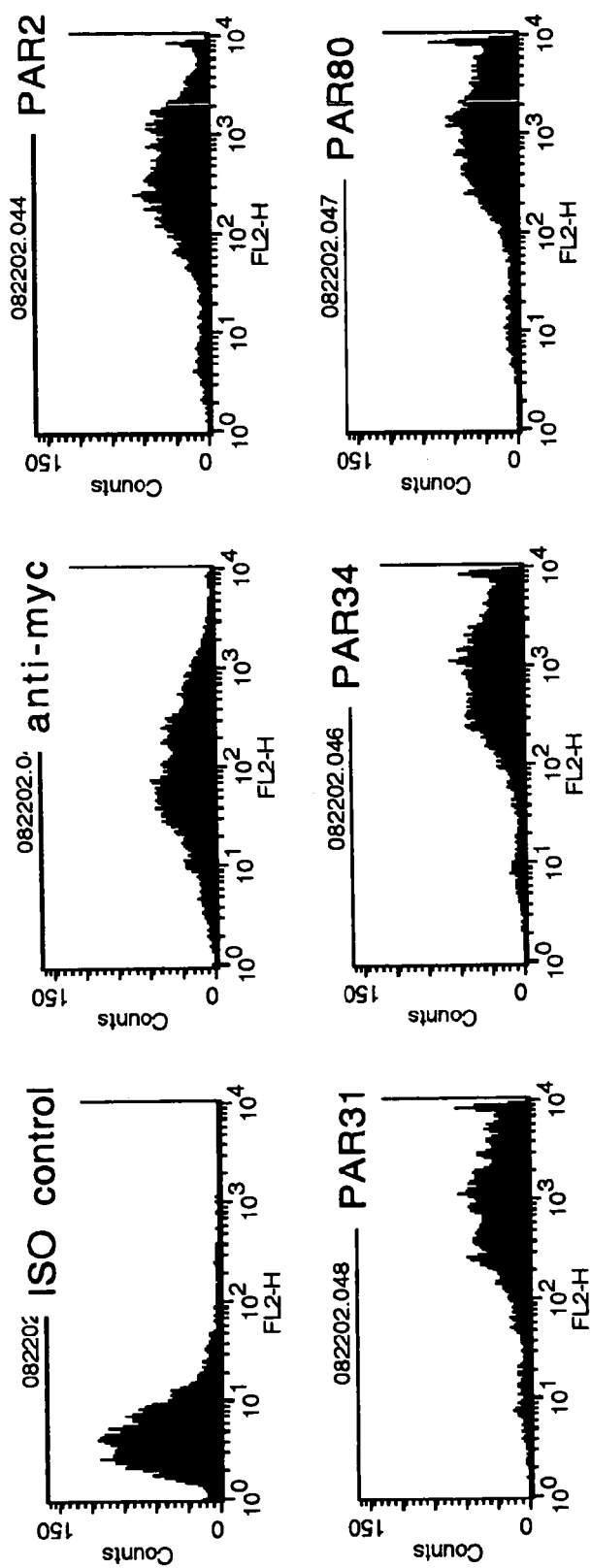
FIG. 3. depicts FACS assays of PAR antibody binding to the surface of cells expressing amphiregulin.

Definitions:

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994–1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:*5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275–1281 (1989); Ward et al., *Nature* 341:544–546 (1989); and Vaughan et al., *Nature Biotech.* 14:309–314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

An antibody having a constant region substantially identical to a naturally occurring class IgG antibody constant region refers to an antibody in which any constant region present is substantially identical, i.e., at least about 85–90%, and preferably at least 95% identical, to the amino acid sequence of the naturally occurring class IgG antibody's constant region.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies useful with the present invention may be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual," Cold Spring Harbor Laboratory Press, New York (1988); Hammerling et al., in: "Monoclonal Antibodies and T-Cell Hybridomas," Elsevier, New York (1981), pp. 563–681 (both of which are incorporated herein by reference in their entireties).

The term "genetically altered antibodies" means antibodies wherein the amino acid sequence has been varied from that of a native antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics. Examples of "genetically altered antibodies" include chimeric and humanized antibodies.

In many preferred uses of the present invention, including in vivo use of the anti-AR antibodies in humans for treatment of cancer or psoriasis, or for in vitro detection assays, it may be preferable to use chimeric, primatized, humanized, or human antibodies.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Methods for producing chimeric antibodies are known in the art. See e.g., Morrison, Science 229:1202–1207 (1985); Oi et al., BioTechniques 4:214–221 (1986); Gillies et al., J. Immunol. Methods 125:191–202 (1989); U.S. Pat. Nos. 5,807,715; 4,816,567; and 4,816,397, which are incorporated herein by reference in their entireties.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85–90%, and preferably at least 95% identical. Hence, all parts of a humanized immunoglobulin, except possibly the CDRs, are substantially identical to corresponding parts of one or more native human immunoglobulin sequences. Accordingly, such humanized antibodies are chimeric antibodies (U.S. Pat. No. 4,816,567), wherein substantially less than an intact human variable domain has been substituted by the corresponding sequence from a non-human species. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693, 761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585, 089), veneering or resurfacing (EP 592,106; EP 519,596; Padlan, Mol. Immunol., 28:489–498 (1991); Studnicka et al., Prot. Eng. 7:805–814 (1994); Roguska et al., Proc. Natl. Acad. Sci. 91:969–973 (1994), and chain shuffling (U.S. Pat. No. 5,565,332), all of which are hereby incorporated by reference in their entireties.

Completely "human" antibodies may be desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.) and Medarex (Princeton, N.J.) can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., Biotechnology 12:899–903 (1988).

The term "primatized antibody" refers to an antibody comprising monkey variable regions and human constant regions. Methods for producing primatized antibodies are known in the art. See e.g., U.S. Pat. Nos. 5,658,570; 5,681, 722; and 5,693,780, which are incorporated herein by reference in their entireties.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996). Two antibodies are said to bind to the same epitope of a protein if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody.

Antibodies of "IgG class" refers to antibodies of IgG1, IgG2, IgG3, and IgG4. The numbering of the amino acid residues in the heavy and light chains is that of the EU index (Kabat, et al., "Sequences of Proteins of Immunological Interest", $5^{th}$ ed., National Institutes of Health, Bethesda, Md. (1991); the EU numbering scheme is used herein).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide are implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "AR" refers to nucleic acid and polypeptide polymorphic variants, alleles, mutants, and interspecies homologues of amphiregulin, including those that: (1) have a nucleotide sequence that has greater than about 60% nucleotide sequence identity, 65%, 70%, 75%, 80%, 85%, 90%, or more preferably 91%, 92%, 93%, 94%, 95%, 96%, 97%, 98% or 99% or greater nucleotide sequence identity, preferably over a region of at least about 25, 50, 100, 200, 500, 1000, or more nucleotides, to a nucleotide sequence encoding the amino acid sequence of SEQ ID NO:1; (2) bind to antibodies, e.g., polyclonal antibodies, raised against an immunogen comprising an amino acid sequence of SEQ ID NO: 1, and conservatively modified variants thereof; (3) specifically hybridize under stringent hybridization conditions to a nucleic acid sequence, or the complement thereof, encoding amino acid sequence of SEQ ID NO: 1 and conservatively modified variants thereof; or (4) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino sequence identity, preferably over a region of at least about 25, 50, 100, 200, or more amino acids, to an amino acid sequence of SEQ ID NO:1. An AR polynucleotide or polypeptide sequence is typically from a mammal including, but not limited to, primate, e.g., human; rodent, e.g., rat, mouse, hamster; cow, pig, horse, sheep, or other mammal. An "AR polypeptide" and a "AR polynucleotide," include both naturally occurring or recombinant forms.

A "full length" AR protein or nucleic acid refers to an ovarian cancer polypeptide or polynucleotide sequence, or a variant thereof, that contains all of the elements normally contained in one or more naturally occurring, wild type AR polynucleotide or polypeptide sequences. For example, a full length AR nucleic acid will typically comprise all of the exons that encode for the full length, naturally occurring protein. The "full length" may be prior to, or after, various stages of post-translation processing or splicing, including alternative splicing.

The term "native form" refers to the correct three-dimensional conformation (i.e. tertiary structure) of a polypeptide as it exists when it is properly and naturally expressed by a cell.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50–100 amino acids or nucleotides in length.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like (see, e.g., the American Type Culture Collection catalog or web site, www.atcc.org).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

"Biological sample" as used herein is a sample of biological tissue or fluid that contains nucleic acids or polypeptides, e.g., of an AR protein, polynucleotide or transcript. Such samples include, but are not limited to, tissue isolated from primates (e.g., humans), or from rodents (e.g., mice, and rats). Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, colloidal gold, luminescent nanocrystals (e.g. quantum dots), haptens and proteins or other entities which can be made detectable, e.g., by incorporating a radiolabel into the peptide or used to detect antibodies specifically reactive with the peptide. The radioisotope may be, for example, $^3H$, $^{14}C$, $^{32}P$, $^{35}S$, or $^{125}I$. In some cases, particularly using antibodies against the proteins of the invention, the radioisotopes are used as toxic moieties, as described below. The labels may be incorporated into the GPR64 nucleic acids, proteins and antibodies at any position. Any method known in the art for conjugating the antibody to the label may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982). The lifetime of radiolabeled peptides or radiolabeled antibody compositions may extended by the addition of substances that stabilize the radiolabeled peptide or antibody and protect it from degradation. Any substance or combination of substances that stablize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin, activatable moieties, a chemotherapeutic or cytotoxic agent, a chemoattractant, a lipase; an antibiotic; or a radioisotope emitting "hard" e.g., beta radiation.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhne-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids, antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming, counterions such as sodium; and/or nonionic surfactants such as TWEEN™, polyethylene glycol (PEG), and PLURONICS™.

A "pharmaceutically effective" or "therapeutically effective" amount, in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of an AR antagonist or anti-AR antibody for purposes of treatment of tumor may be determined empirically and in a routine manner.

"Treatment" refers to both therapeutic treatment and prophylactic or preventative measures. Those in need of treatment include those already with the disorder as well as those in which the disorder is to be prevented.

A "subject" refers to a vertebrate, preferably a mammal, more preferably a human.

The term "cancer" refers to any type of physiological condition found in mammals typically characterized by unregulated cell growth (e.g. neoplasm or malignant tumor) including carcinomas, lymphomas, blastomas, sarcomas, or hematopoietic neoplastic disorders. Examples of cancers include, but are not limited to, Hodgkin's Disease, Non-Hodgkin's Lymphoma, multiple myeloma, leukemia, neuroblastoma, breast cancer, ovarian cancer, lung cancer, cancers of head and neck, cancer of endothelium, cancers of bone, cancers of muscle, pancreatic cancer, rhabdomyosarcoma, primary thrombocytosis, primary macroglobulinemia, small-cell lung tumors, stomach cancer, colon cancer, kidney cancer, malignant pancreatic insulanoma, malignant carcinoid, urinary bladder cancer, melanoma, premalignant skin lesions, testicular cancer, lymphomas, thyroid cancer, esophageal cancer, genitourinary tract cancer, malignant hypercalcemia, cervical cancer, endometrial cancer, epidermal cancer, adrenal cortical cancer, prostate cancer, or uterine cancer. Cancer cells are the cancerous cells of any type of cancers, which can be cells of cancer tissues from a patient or cells of an established cancer cell line.

"Tumor", as used herein, refers to all neoplastic cell growth and proliferation, whether malignant or benign, and all pre-cancerous and cancerous cells and tissues.

I. The Amphiregulin (AR) Polypeptides

The term "amphiregulin" and "the amphiregulin polypeptide" are used interchangeable herein, which refer to a full-length AR protein or a functionally active fragment or derivative thereof. Active forms of amphiregulin are generated from an internal cleavage product of an internal membrane protein precursor. Examples of these active forms are AR84, AR87, or AR98. The 252 amino acid sequence of human AR (GenBank Accession no. NP_001648) is as follows:

also include those fragments that comprise one or more structural domains of a AR polypeptide, such as a binding domain. Protein domains can be identified using the PFAM program (Bateman A., et al., Nucleic Acids Res. 27: 260–2 (1999)).

AR polypeptide derivatives typically share a certain degree of sequence identity or sequence similarity with SEQ ID NO:1 or a fragment thereof. AR derivatives can be produced by various methods known in the art, such as cleavage by restriction enzymes or mutagenesis.

II. Antagonists of AR

The antagonists of AR include any molecules that directly or indirectly counteract, reduce, or inhibit AR biological activities. In a preferred embodiment, the antagonists of AR compete or preferably block the binding of AR to their receptors, such as EGFR. The antagonists should counteract, reduce, or inhibit at least one biological activity of AR, for example, the receptor binding, the tyrosine phosphorylation, the down-stream signal transduction, the mitogenic activities, the proliferation of cells in psoriasis lesion.

In a preferred aspect, the antagonists directly interact with AR. Preferably, the antagonists are proteins. More preferably, the proteins bind to AR, and even more preferably, the antagonists are antibodies including antibody fragments that bind to AR and neutralize at least one biological activity of AR.

In another aspect, the antagonists are any polypeptides or peptides that inhibit AR activities but do not directly interact with AR. In one aspect, these antagonists block the binding of AR to its receptors, such as EGFR. For example, the antagonists can be mutated AR molecules, such as dominant-negative mutants derived from a wild-type AR by terminal truncation or amino acid substitution. Preferably such mutated ARs retain the binding ability to the signaling molecules of AR but lose the ability of triggering the downstream signaling trasnduction of AR. Therefore, the mutated AR molecules can compete with the wild-type AR and thus block the activities of the wild-type AR. The standard mutagenesis and molecular cloning techniques can accomplish the terminal truncation and amino acid substitution. The mutated AR molecules can be administered into the target cells by standard delivery means known in the art, such as, lipid or viral transfections. Additional examples are antibodies or other peptide blockers that block the ligand-binding site with AR of the receptors of AR. Exemplary antibodies are the antibodies against EGFR.

```
MRAPLLPPAP VVLSLLILGS GHYAAGLDLN DTYSGKREPF SGDHSADGFE    (SEQ ID NO:1)

VTSRSEMSSG SEISPVSEMP SSSEPSSGAD YDYSEEYDNE PQIPGYIVDD

SVRVEQVVKP PQNKTESENT SDKPKRKKKG GKNGKNRRNR KKKNPCNAEF

QNFCIHGECK YIEHLEAVTC KCQQEYFGER CGEKSMKTHS MIDSSLSKIA

LAAIAAFMSA VILTAVAVIT VQLRRQYVRK YEGEAEERKK LRQENGNVHA IA
```

A functionally active AR fragment or derivative exhibits one or more functional activities associated with a full-length, wild-type AR protein, such as antigenic or immunogenic activity, ability to bind natural cellular substrates, etc. The functional activity of AR proteins, derivatives and fragments can be assayed by various methods known to one skilled in the art (Current Protocols in Protein Science Coligan et al., eds., John Wiley & Sons, Inc., Somerset, N.J. (1998)). For purposes herein, functionally active fragments Alternatively, the antagonists interact with and regulate the up-stream or downstream components of the AR signaling pathway and indirectly reduce the activities of AR. For example, it is known that AR activities are mediated through the receptor tyrosine kinase pathway upon its binding to the EGF receptors. Accordingly, any molecules capable of regulating this pathway can be candidate antagonists, including, but not limited to, the antibodies or other antagonist blocking the binding and activities if the components of EGF receptor signaling pathway known in the art. Yeast two-hybrid and variant screens offer preferred methods for identifying endogenous additional interacting proteins of AR signaling pathways (Finley, R. L. et al. in DNA Cloning-Expression Systems: A Practical Approach, eds. Glover D. & Hames B. D. (Oxford University Press, Oxford, England), pp. 169–203 (1996); Fashema S. F. et al., Gene 250: 1–14 (2000); Drees B.L., CUK Opin Chem Biol 3: 64–70 (1999); Vidal M. and Legrain P. Nucleic Acids. Res. 27:9191–29 (1999); and U.S. Pat. No. 5,928,868). Mass spectrometry is an alternative method for the elucidation of protein complexes (reviewed in, e.g., Pandley A and Mann M, Nature 405: 837–846 (2000); Yates J R 3rd, Trends Genet 16: 5–8 (2000)).

In yet another aspect, the antagonists should inhibit the protein expression of AR. AR expression can be regulated at the level of transcription, such as, by a regulator of transcription factors of AR, or at the level of mRNA splicing, translation or post-translation.

The antagonists can also be nucleic acids, including, but not limited to, anti-sense nucleic acids of the nucleic acid sequence encoding part or full or having substantial sequence similarity of AR. The DNA sequence of AR is known in the art and disclosed herein. Subsequently, anti-sense nucleic acid probes of AR DNA, and the optimal condition of the anti-sense blocking can be developed by using the related techniques known to a skilled artisan in the field of molecular biology. Similarly, the nucleic acid reagent may belong to the class of micro-RNA (mRNA), short-hairpin RNA (shRNA) or short interfering RNA (siRNA) (See e.g. Ambros, *Cell* 113: 673 (2003); Bartel and Bartel, *Plant Physiol.* 132: 709 (2003); and Palatnik et al., *Nature* 425; 257 (2003)).

The antagonists of the present invention also include small molecules, which often modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of antagonists includes chemically synthesized molecules, for instance, compounds from combinatorial chemical libraries. Synthetic compounds may be rationally designed or identified based on known or inferred properties of the AR protein or may be identified by screening compound libraries. Alternative appropriate antagonists of this class are natural products, particularly secondary metabolites from organisms such as plants or fungi, which can also be identified by screening compound libraries for AR-modulating activity. Methods for generating and obtaining compounds are well known in the art (Schreiber S L, Science 151: 1964–1969 (2000); Radmann J and Gunther J, Science 151: 1947–1948 (2000)).

III. Antibodies Against AR

The antibodies against AR (i.e. anti-AR antibodies) of the present invention may be in a polyclonal or monoclonal form and should bind to at least one epitope of AR, preferably a human AR, and more preferably, at least one of the human biologically active forms of AR. The antibodies should bind to a) a partial or full-length AR protein, or b) a functionally active fragment or derivative thereof. The antibodies include antibodies having all types of constant regions, including IgM, IgG, IgD, IgA and IgE, and any isotype, including IgG1, IgG2a, IgG2b, IgG3 and IgG4. The light chain can be kappa or lambda light chain.

In a preferred aspect, anti-AR antibodies preferably bind to an AR epitope at a binding affinity of at least $10^6 M^{-1}$, $10^7 M^{-1}$, $10^8 M^{-1}$, $10^9 M^{-1}$ or $10^{10} M^{-1}$.

In a more preferred aspect, the antibodies of the present invention neutralize at least one biological activities of AR, such as receptor binding activities, signaling transductions, and cellular responses. These neutralizing antibodies are capable of competing with the binding of AR to its receptors, or even block the binding completely. These antibodies should inhibit or completely neutralize signaling activities, and/or induction of cellular responses, for example, tyrosine phosphorylation, and/or AR-mediated cell proliferation. In one example, the neutralizing antibodies are capable of inhibiting proliferation of the types of cells wherein AR is endogenously expressed, such as murine 3T3 and human HEKn cells. Preferably, a concentration of 0.005, 0.01, 0.05, 0.1, 0.25, 0.5, 1, 2, 5, 10, or 100 μg/ml of the antibodies will block at least 10%, 25%, 50%, 90%, 95%, 99% or essentially 100% of the binding of AR to EGFR or AR-mediated cell proliferation, especially when the AR is also used at one of these concentrations or at a molar concentration that is 0.005, 0.01, 0.05, 0.1, 0.25, 0.5 or 1.0 of the concentration of the antibody.

Exemplary neutralizing antibodies, also described in the Examples below and listed in the table depicted in FIG. 2, include the following monoclonal antibodies: PAR2, PAR5, PAR15, PAR19, PAR22, PAR23, PAR26, PAR29, PAR31, PAR34, PAR44, PAR46, PAR51, PAR67, PAR79, PAR80, PAR81, and PAR84. These antibodies bind to the AR expressed on cell surfaces. Almost all of them inhibit, or even complete block the AR-mediated proliferation of murine 3T3 cells or human HEKn cells. PAR34 and PAR80 have the most potent neutralizing capability. As little as 0.072 μg/ml PAR34 and PAR80 inhibit AR-mediated 3T3 cell proliferation by abut 50%. PAR2, PAR 5, PAR15, PAR23, PAR46, PAR84 are also very potent neutralizing antibodies. The amino acid sequence of the mature heavy chain and light chain variable region of PAR34 are presented here in SEQ ID NOs:2 and 3 respectively. The amino acid sequence of the mature heavy chain and light chain variable region of PAR80 are presented here in SEQ ID NOs:4 and 5 respectively.

The present invention provides for anti-AR antibodies comprising a mature heavy chain variable region comprising an amino acid sequence selected from SEQ ID NOs: 2, 4, and 12. These antibodies may further comprise a mature light chain variable region comprising amino acid sequence selected from SEQ ID NOs: 3, 5 and 14. The present invention includes antibodies that bind to the same epitope of these antibodies. The determination of epitope type is accomplished by methods known in the art, such as a competition assay, which, for example, may be detected by changes in fluorescence intensity as measured by flow cytometry. In cases where the epitopes of the two antibodies are similar, the antigen-binding sites will be occupied by the first antibody and the second antibody conjugate will be unable to bind cells. This results in loss of signal of this conjugate, so that the fluorescence intensity will be reduced.

The present invention includes the analogs of the antibodies describes herein. Preferred analogs include antibodies comprising heavy chain variable regions having about at least 60%, 80% or 90–95% amino acid sequence identity of SEQ ID NOs: 2, 4, and 12 and/or comprising mature light chain variable regions having about at least 60%, 80% or 90–95% amino acid sequence identity of SEQ ID NOs:3, 5 and 14.

Methods of determining percent identity are known in the art. "Percent (%) sequence identity" with respect to a specified subject sequence, or a specified portion thereof, may be defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. 215: 403–410 (1997); http://blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. Any two antibody sequences can only be aligned in one way, by using the numbering scheme in Kabat ("Sequences of Proteins of Immunological Interest" Kabat, E. et al., U.S. Department of Health and Human Service (1983)). Therefore, for antibodies, percent identity has a unique and well-defined meaning. A "% identity value" is determined by the number of matching identical nucleotides or amino acids divided by the sequence length for which the percent identity is being reported.

Additional preferred analogs of exemplified antibodies differ from exemplified antibodies by conservative amino acid substitutions. For purposes of classifying amino acids substitutions as conservative or nonconservative, amino acids may be grouped as follows: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Antibodies against AR of all species of origins are included in the present invention. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. In a preferred embodiment, the antibody is an isolated monoclonal antibody that binds to or neutralizes AR.

The monoclonal antibodies are produced by conventional hybridoma methodology known in the art. The hybridoma technique described originally by Kohler and Milstein, Nature 256: 495–7 (1975); Eur. J. Immunol. 6: 511 (1976)) has been widely applied to produce hybrid cell lines that secrete high levels of monoclonal antibodies against many specific antigens.

The polyclonal forms of the anti-AR antibodies are also included in the present invention. Preferably, these antibodies neutralize at least one activities of AR, or bind to the epitopes that the described monoclonal antibodies bind to in the present invention. The polyclonal antibody can be produced by immunization of host animals by AR or the fragments thereof. The polyclonal antibodies are secreted into the bloodstream and can be recovered using known techniques. Purified forms of these antibodies can, of course, be readily prepared by standard purification techniques, preferably including affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

Genetically-altered (i.e. recombinant) antibodies against AR are also included in the present invention. These recombinant antibodies have the same amino acid sequence as the natural antibodies or have altered amino acid sequences of the natural antibodies in the present invention. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

The genetically altered anti-AR antibodies should be functionally equivalent to the above-mentioned natural antibodies and recombinant antibodies. Modified antibodies providing improved stability and/or therapeutic efficacy are preferred. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as-long as the therapeutic utility is maintained. Antibodies of this invention can be modified post-translationally (e.g., acetylation, and phosphorylation) or can be modified synthetically (e.g., the attachment of a labeling group, such as a cytotoxic agent). Preferred genetically altered antibodies are chimeric antibodies and humanized antibodies.

The present invention includes a chimeric antibody comprising a variable region derived from a mouse and a constant region derived from human, so that the chimeric antibody has a longer half-life and is less immunogenic when administered to a human subject. In one embodiment, the murine variable regions are derived from any one of the monoclonal antibodies described herein, including the non-limiting examples: a) the monoclonal antibodies comprising a mature heavy chain variable region comprising amino acid sequence selected from SEQ ID NOs:2 and 4 and/or a mature light chain variable region comprising amino acid sequence selected from SEQ ID NOs:3 and 5; b) the antibodies that bind to the same epitope of a); or c) the analogs of a).

In order to produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making the chimeric antibody is disclosed in U.S. Pat. No. 5,677,427; U.S. Pat. No. 6,120,767; and U.S. Pat. No. 6,329,508, each of which is incorporated by reference in its entirety.

The genetically altered antibodies of the present invention also include humanized antibodies that bind to or neutralize AR. Methods of making humanized antibody are disclosed in U.S. Pat. Nos. 5,530,101; 5,585,089; 5,693,761; 5,693,762; and 6,180,370 each of which is incorporated by reference in its entirety. In one embodiment of the present invention, the humanized antibody comprises CDRs of a mouse donor immunoglobulin and heavy chain and light chain frameworks of a human acceptor immunoglobulin.

For example, the humanized versions of a) the monoclonal antibodies comprising a mature heavy chain variable region comprising amino acid sequence of SEQ ID NOs:2 or 4 and/or a mature light chain variable region comprising amino acid sequence of SEQ ID NOs:3 or 5; b) the antibodies that bind to the same epitope of a); or c) the analogs of a). Example 6, disclosed herein describes the humanization of monoclonal antibody PAR34 to yield a HuPAR34 with a amino acid sequence comprising SEQ ID NOs: 12 and 14.

Anti-AR primatized or fully human antibodies are also included in the present invention. In a preferred embodiment of the present invention, said primatized or fully human antibodies neutralize the activities of AR described herein.

Fully human antibodies against AR are produced by a variety of techniques. One example is trioma methodology. The basic approach and an exemplary cell fusion partner, SPAZ-4, for use in this approach have been described by Oestberg et al., Hybridoma 2:361–367 (1983); Oestberg, U.S. Pat. No. 4,634,664; and Engleman et al., U.S. Pat. No. 4,634,666 (each of which is incorporated by reference in its entirety)

Human antibodies against AR can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, one approach is to screen a DNA library from human B cells according to the general protocol outlined by Huse et al., Science 246:1275–1281 (1989). Antibodies binding AR or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety). In these methods, libraries of phage are produced in which members display different antibodies on their outer surfaces. Antibodies are usually displayed as Fv or Fab fragments. Phage displaying antibodies with a desired specificity are selected by affinity enrichment to AR or fragment thereof.

Eukaryotic ribosome can also be used as a mean to display a library of antibodies and isolate the binding human antibodies by screening against the target antigen, such as AR, as described in Coia G, et al., J. Immunol. Methods 1: 254 (1–2): 191–7 (2001); Hanes J. et al., Nat. Biotechnol.: 18(12): 1287–92 (2000); Proc. Natl. Acad. Sci. U.S.A. 95(24): 14130–5 (1998); Proc. Natl. Acad. Sci. U.S.A. 94(10): 4937–42 (1997), each of which in incorporated by reference in its entirety.

Yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212–20 (2002); Boeder, E. T., et al., Nat. Biotechnol. 15(6):553–7 (1997), each of which is herein incorporated by reference in its entirety. Alternatively, human antibody libraries may be expressed intracellularly and screened via yeast two-hybrid system (WO0200729A2, which is incorporated by reference in its entirety).

Fragments of the anti-AR antibodies, which retain the binding specificity to AR, are also included in the present invention. Examples include, but are not limited to, partial or full heavy chains or light chains, variable regions, or CDR regions of any anti-AR antibodies described herein.

In a preferred embodiment of the invention, the antibody fragments are truncated chains (truncated at the carboxyl end). Preferably, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemistry techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining $V_L$ and $V_H$ coding regions with a DNA that encodes a peptide linker connecting the VL and VH protein fragments Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins (e.g., immunotoxins) or conjugates having novel properties.

The present invention comprises the use of anti-AR antibodies conjugated to various effector moieties including but not limited to immunotoxins. Conjugates that are immunotoxins including antibodies have been widely described in the art. The toxins may be coupled to the antibodies by conventional coupling techniques or immunotoxins containing protein toxin portions can be produced as fusion proteins. The conjugates of the present invention can be used in a corresponding way to obtain such immunotoxins. Illustrative of such immunotoxins are those described by Byers, B. S. et al., Seminars Cell Biol 2:59–70 (1991) and by Fanger, M. W. et al., Immunol Today 12:51–54 (1991).

Recombinant DNA techniques can be used to produce the recombinant anti-AR antibodies, as well as the chimeric or humanized anti-AR antibodies or any other anti-AR genetically-altered antibodies and the fragments or conjugate thereof in any expression systems including both prokaryotic and eukaryotic expression systems, such as bacteria, yeast, insect cells, plant cells, mammalian cells (for example, NSO cells).

Once produced, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extra corporeally) or in developing and performing assay procedures, immunofluorescent stainings, and the like. (See, generally, Immunological Methods, Vols. I and II (Lefkovits and Pernis, eds., Academic Press, NY, 1979 and 1981).

IV. Therapeutic Methods

AR antagonists, preferably anti-AR antibodies are useful in cancer prevention or treatment. In one preferred aspect, the present invention provides for a method of inhibiting the proliferation of cancer cells comprising contacting the cancer cells with the AR antagonists described herein, preferably, anti-AR antibodies described herein. The antagonists contact with cancer cells in vitro, ex vivo or in vivo (such as in a subject, preferably in a mammal, and more preferably in a human). Preferably, the present invention provides for a method of inhibiting cancer cell growth in a subject comprising administering an AR antagonist, preferably an anti-AR antibody, into the subject in a pharmaceutically effective amount. In one example, the cancer cells are the pancreatic cancer cells or/and epidermal cancer cells. The anti-AR antibodies include the antibodies, antibody fragments, and antibody conjugates of the present invention, preferably, the antibodies having potent neutralizing activities, such as the antibodies comprising the amino acid sequences described herein and their chimeric or humanized version. Such an inhibition reduces the cancer cell proliferation by at least 10%, 30%, 50%, 70%, 80%, or 90%.

The inhibition of the antibodies on the cancer cell proliferation can be measured by cell-based assays, such as bromodeoxyuridine (BRDU) incorporation (Hoshino et al., Int. J. Cancer 38, 369 (1986); Campana et al., J. Immunol. Meth. 107:79 (1988)); [$^3$H]-thymidine incorporation (Chen, J., Oncogene 13:1395–403 (1996); Jeoung, J., J. Biol. Chem. 270:18367–73(1995); the dye Alamar Blue (available from Biosource International) (Voytik-Harbin SL et al., In Vitro Cell Dev Biol Anim 34:239–46 (1998)); colony formation assay in soft agar (Sambrook et al., Molecular Cloning, Cold Spring Harbor, 1989).

The inhibition is also assessed via tumorigenicity assays. In one example, a xenograft comprises human cells from a pre-existing tumor or from a tumor cell line. Tumor xenograft assays are known in the art (see, e.g., Ogawa K et al., Oncogene 19:6043–6052 (2000)). In another preferred embodiment, tumorogenicity is monitored using a hollow fiber assay, which is described in U.S. Pat. No. 5,698,413, which is incorporated by reference in its entirety.

The above-described methods of the present invention inhibit, reverse cancer cell proliferation, or metastasis, or reduce the size of cancer in said subject.

Examples 3–5 and 7 disclosed herein exemplify assays demonstrating inhibition of AR activity (including effects on cell proliferation and xenograft tumor growth) by anti-AR antibodies.

In another preferred aspect, the antagonists, preferably antibodies of the present invention can be used for the treatment of psoriasis. Psoriasis is one of the most common skin diseases, affecting up to 2 percent of the world population. It is a chronic inflammatory skin disorder clinically characterized by erythematous, sharply demarcated papules and rounded plaques covered by silvery micaceous scales. The skin lesions of psoriasis are variably pruritic. Traumatized areas often develop lesions of psoriasis (Koebner or isomorphic phenomenon). Additionally, other external factors may exacerbate psoriasis including infections, stress, and medications (e.g., lithium, beta blockers, and antimalaria medications) (Harrison's Principles of Internal Medicine, 14th Edition, pp. 300 (1998)). The severity of psoriasis is measured by the Psoriasis Area Severity Index (PASI) (see e.g., Fleischer et al. (1999), J. Dermatol. 26:210–215 and Tanew et al. (1999), Arch Dermatol. 135: 519–524) or various psoriasis global assessment scores such as Physician's Global Assessment (PGA) which are well-known to those skilled in the art of treating psoriasis.

The present invention provides for a method of treating psoriasis in a subject in need of such a treatment comprising administering a pharmaceutically effective amount of a antagonist of AR to said subject. Preferably, said antagonist is an anti-AR antibody, more preferably, the antibodies and antibody fragments, and conjugates disclosed herein.

Example 8 disclosed herein exemplifies an in vivo study where anti-AR antibody (HuPAR34) is used treat psoriatic skin transplant in SCID mice.

In another aspect of the present invention, the antagonists, preferably antibodies described herein can be used for the would healing, enhancing skin qualities, or providing benefit to any other disorders caused by the abnormal hyperactivity of AR.

Therapeutic methods are usually applied to human patients but may be applied to other mammals.

There are various methods of administering the antagonists, for example, antibodies of the present invention. Parenteral administration is preferred. The antibody may be administered to a patient intravenously as a bolus or by continuous infusion over a period of time; or by intramuscular, subcutaneous, intraperitoneal, or intra-cerebrospinal routes. Oral, topical, inhalation routes, or other delivery means known to those skilled in the art are also included in the present invention.

The pharmaceutical compositions of the present invention commonly comprise a solution of antagonists (for example, antibodies), or a cocktail thereof dissolved in an acceptable carrier, preferably an aqueous carrier. That is, the antibodies can be used in the manufacture of a medicament for treatment of patients. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make isotonic. The carrier can also contain excipients such as human serum albumin, polysorbate 80, sugars or amino acids to protect the active protein. The concentration of an antagonist (for example, antibody) in these formulations varies widely from about 0.1 to 100 mg/ml but is often in the range 1 to 10 mg/ml. The formulated monoclonal antibody is particularly suitable for parenteral administration, and can be administered as an intravenous infusion or by subcutaneous, intramuscular or intravenous injection. Actual methods for preparing parentally administrable compositions are known or apparent to those skilled in the art and are described in more detail in, for example, Remington's Pharmaceutical Science (15th Ed., Mack Publishing Company, Easton, Pa., 1980), which is incorporated herein by reference. The present invention provides for a pharmaceutical composition comprising an antibody that binds to AR, preferably one of the antibodies described herein.

The compositions can be administered for prophylactic and/or therapeutic treatments. An amount adequate to accomplish the desired effect is defined as a "pharmaceutically effective amount". The antagonists (such as antibodies) can be delivered into a patient by single or multiple administrations. Doses of the drug for psoriasis will typically contain from 0.01 to 100 mg antagonist (for example, antibody or fusion protein) but most often from 0.1 to 1, or 1, 2 or 5 to 20 mg per kilogram body weight or as a unit dose, in an amount sufficient to alleviate the disease without causing unacceptable side effects ("pharmaceutically effective dose"). The antibody drug may be administered once or multiple times, e.g., 1, 2 or 3 times per day, week or month for one to several days, weeks, months or years, or chronically, depending upon the nature and severity of the disease.

For the purpose of treatment of disease, the appropriate dosage of the antagonists (for example, antibodies) will depend on the severity and course of disease, the patient's clinical history and response, the toxicity of the antibodies, and the discretion of the attending physician. The antagonists are suitably administered to the patient at one time or over a series of treatments. The initial candidate dosage may be administered to a patient. The proper dosage and treatment regimen can be established by monitoring the progress of therapy using conventional techniques known to the people skilled of the art.

Additionally, the antagonist (such as antibodies) can be utilized alone in substantially pure form, or together with therapeutic agents, as are known to those of skill in the art (see, e.g., Cancer: Principles and Practice of Oncology, 5$^{th}$ ed., Devita et al., Lippincott-Ravel Publishers, 1997). Other therapies that may be used in conjunction with treatment with the antibodies include administration of anti-sense nucleic acid molecules or biologicals, such as additional therapeutic antibodies. Thus, the treatment of the present invention is formulated in a manner allowing it to be administered serially or in combination with another agent for the treatment of cancer or psoriasis. For the treatment of psoriasis, the antibody will often be administered after or in combination with one or more other immunosuppressive drugs or other therapies, for example, corticosteroids, cyclosporine, methotrexate, phototherapy (with or without PUVA). For the treatment of cancer, the conventional therapeutic methods for cancer therapy, such as chemotherapy, radiation therapy and surgery can be used together with the antagonists.

V. Diagnostic Methods

Antibodies disclosed herein are useful in diagnostic and prognostic evaluation of diseases and disorders, particularly cancers or psoriasis associated with AR expression. At each stage of disease, monoclonal antibodies may be used to improve diagnostic accuracy and facilitate treatment decisions.

Methods of diagnosis can be performed in vitro using a cellular sample (e.g., blood sample, lymph node biopsy or tissue) from a patient or can be performed by in vivo imaging.

In particular embodiments, the present invention provides an antibody conjugate wherein the antibodies of the present invention are conjugated to a diagnostic imaging agent. Compositions comprising the antibodies of the present invention can be used to detect AR, for example, by radioimmunoassay, ELISA, FACS, etc. One or more labeling moieties can be attached to the antibodies. Exemplary labeling moieties can include radiopaque dyes, radiocontrast agents, fluorescent molecules, spin-labeled molecules, enzymes, or other labeling moieties of diagnostic value, particularly in radiologic or magnetic resonance imaging techniques.

The present invention provides for a method of detecting a cancer or psoriasis comprising detecting the differential expression of mRNA or protein of AR in said cancer or psoriasis cells in a subject in need of such detection.

In one exemplary embodiment, the method of detecting cancer comprising: a) isolating a sample from a patient; b) contacting cells of said sample with the antibodies of the present invention; c) contact non-cancerous cells of the same type of cells of said sample cells with the antibodies of the present invention; and d) detecting and comparing the difference of expression of AR in said sample cells with the non-cancerous cells.

In another exemplary embodiment, the method of detecting psoriasis comprising: a) isolating a skin sample from a patient; b) contacting cells of said skin sample with the antibodies of the present invention; c) contact normal skin cells with the antibodies of the present invention; and d) detecting and comparing the difference of the expression of AR in said skin sample cells with the said normal skin cells.

In addition to detecting the cancer or psoriasis at pre- or early disease stage, the antibodies of the present invention can also be used to evaluate the treatment efficacy of a therapeutic approach, such as a method of treating psoriasis. Antibodies are utilized to detect the expression level of AR before and after certain treatment. Reduction in AR expression level may be an indicator of the effectiveness of the treatment.

The antibodies of the present invention can also be used as detecting agents for the in vitro assays for research purposes. For example, the antibodies can be used to identify or isolate the novel receptors or other binding proteins for AR via the methods known in the art, such as by screening protein expression libraries.

The present invention also provides for a diagnostic kit comprising anti-AR antibodies. Such a diagnostic kit further comprises a packaged combination of reagents in predetermined amounts with instructions for performing the diagnostic assay. Where the antibody is labeled with an enzyme, the kit will include substrates and co-factors required by the enzyme. In addition, other additives may be included such as stablizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

Though the antibodies of the present invention are primarily concerned with the treatment of human subjects, they may also be employed for the treatment of other mammalian subjects such as dogs and cats for veterinary purposes.

The following examples are offered by way of illustration and not by way of limitation. The disclosures of all citations in the specification are expressly incorporated herein by reference in their entirety.

EXAMPLES

Example 1

Generation of Soluble AR Proteins

This example describes the generation of soluble proteins of AR. Constructs were made for the recombinant expression of the human AR. The wild-type full-length human AR polypeptide (SEQ ID NO:1) and other cloned AR forms were cloned by PCR.

Three constructs were generated to aid in further characterization of the anti-human amphiregulin monoclonal antibodies. The constructs included mammalian expression plasmids for soluble AR, soluble human IgG3 Fc fusion protein, and cell surface expression. For cell surface expression, plasmid construct was created so that the C-terminus of AR is fused with a GPI membrane anchor.

PCR reactions were carried out using human-specific primers, the human cDNA as the template, and cloned pfu DNA polymerase (Roche) according to manufacturer's instructions. The resulting PCR DNA fragments encoding human AR were then ligated with expression vectors pDL174 (soluble), pDL182 (human IgG3 Fc fusion protein), and pDL301 (cell surface) (PDL) to generate pDL389, pDL390, and pDL391 respectively. The nucleotide sequences of the AR portion in each of the plasmids were confirmed by DNA sequencing.

The 293H and Cos-7 cell lines were grown according to the supplier's instructions (ATCC). Plasmid DNAs of AR expressing proteins were transfected into 293H cells using TransIT-293 (Fisher) transfection reagent according to the manufacturer's instructions for secreted proteins. Culture media were harvested 3–5 days later, and the expressed AR fusion proteins were purified by affinity, column chromatography. Plasmid DNA for cell surface expression was transfected into Cos-7 cells using Lipofectamine2000® transfection formulation (Life Technologies). Cells were analyzed for surface expression and cloned.

The soluble AR fusion protein was purified from supernatants of the transfected cells via an affinity column using one of the produced anti-AR antibodies, the PAR5 antibody. The human IgG3 fusion protein was purified using a protein G column.

Example 2

Generation of Anti-AR Monoclonal Antibodies

This example describes the production of anti-AR monoclonal antibodies.

Immunogens for AR

Recombinant human AR was purchased from R&D Systems and used to immunize Balb/c mice via either the intraperitoneal or footpad route. Briefly, mice were immunized intraperitoneally or in the hind footpads using 5–20 μg protein with an equal volume of Ribi adjuvant in a total final volume of 20 μl. Footpad immunizations were performed 4 times at 4 or 5-day intervals. Intraperitoneal immunization involved 4 immunizations at two-week intervals.

ELISA: Pre- and Post-Immunization

Serum titers were determined by ELISA against human recombinant AR using a standard antibody capture ELISA assay and peroxidase mediated detection. Serial dilutions of both pre-immune and post-immune serum were incubated with the capture protein and antigen-antibody complexes were detected using a horseradish peroxidase conjugated anti-mouse IgG secondary antibody and chromogenic reagent. Quantification of protein specific serum titer was determined spectrophotometrically ($A_{415}$).

Sera were also examined for reactivity against EGF and HB-EGR (R & D Systems) to determine specificity of the immune response.

Fusion

Mice with highest sera titers against the AR fusion protein, and no detectable reactivity against EGF and HB-EGF, were sacrificed. The popliteal, femoral and sacral lymph nodes were removed from footpad immunized mice, and the spleens were removed from intraperitoneally immunized mice. Lymphocytes were isolated from the tissues, and hybridomas were generated by standard procedures. Briefly, hybridomas were generated by polyethylene glycol (PEG) 1500 mediated fusion between lymphocytes and a murine myeloma cell line (NSO cells). Fused cells were plated into 96 well plates at a density of $10^5$ cells per plate. Selection of fused cells was accomplished using HAT (hypoxanthine, aminopterin, thymidine) media.

Screening the Hybridomas

Specificity of antibodies secreted by hybridomas was initially determined by an ELISA using human recombinant AR as described above. Supernatants from hybridoma wells were incubated in wells coated with recombinant human AR. Detection and quantitation of antigen-antibody interaction were achieved using the same methods as described above. Detection of positive wells was interpreted as hybridomas secreting a monoclonal antibody likely to have specificity for human AR.

Specificity of antibodies for human AR was confirmed by examining all supernatants positive for binding to AR for reactivity with EGF and HB-EGF by ELISA. No supernatants exhibited reactivity with these proteins that, like AR are members of the EGF family. Reactivity of antibodies with AR proteins likely to be expressed in a native conformation was further determined by testing hybridoma supernatants on ELISA plates coated with goat anti-human AR antibody that had been incubated with the supernatant of PMA-stimulated MCF-7 cells, which contains soluble native human AR. Binding to captured MCF-7-derived AR established reactivity with native, mammalian cell-derived human AR. The specificity of ELISA positive supernatants for "native" cell surface AR was evaluated using standard flow cytometry methods on a CHO cell line transfected with full-length cell surface human AR.

Flow cytometry was performed by using the protocol known in the art. In particular, CHO transfectants expressing surface AR ($2\times10^5$) were resuspended in 50 μL ice cold PBS with 10–100 μL hybridoma supernatant on ice for 1 hour. After extensive washing, cells were incubated with phycoerythrin-conjugated goat antibodies specific for mouse IgG for 60 minutes on ice. Cells were washed again and cell surface bound antibody was detected by flow cytometry using a Becton Dickinson FACScan. Hybridomas considered to be positive for the target antigen were interpreted as those that give at least one logarithmic shift in fluorescence above the background negative control. As shown in FIG. 3, antibodies such as PAR2, PAR31, PAR34, and PAR80 are capable of binding to native forms of AR.

Additional screenings with the various ELISAs and flow cytometry analysis of three hybridoma fusions were carried out (two on footpad immunized mice, one on mice immunized intraperitoneally) and gave rise to 84 positive clones for human AR. The table depicted in FIG. 2 summarizes some of the positive monoclonal antibodies, their isotypes, binding characteristics, and neutralizing capability.

Example 3

Anti-AR Antibody Inhibition Assay

This example describes the anti-AR antibody inhibition of binding between AR and EGF receptors.

Figure 4:
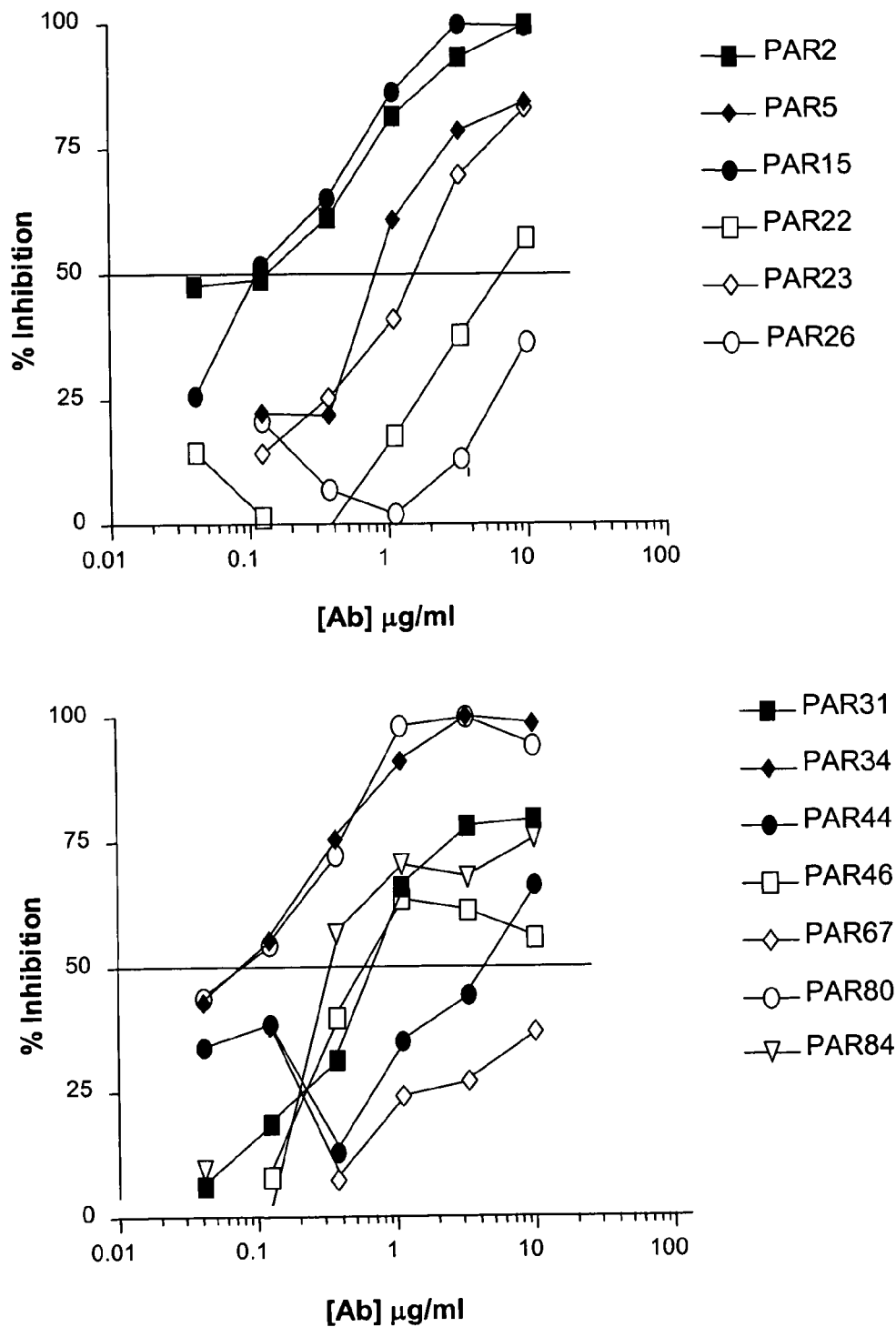
FIG. 4 depicts plots of in vitro PAR antibody neutralization of amphiregulin

Human recombinant AR (2 μg/ml) was incubated for 30 minutes on ice with supernatants of hybridoma cells that had previously demonstrated binding to human AR by ELISA. This mixture was then added to $1\times10^6$ A431 cells (expressing high level of EGF-R), and incubated for an additional 60 minutes on ice. The cells were then washed, and incubated with biotin-labeled goat antibodies specific for human AR for 30 minutes on ice. Cells were washed, incubated with phycoerythrin-conjugated avidin, and incubated for another 30 minutes on ice. Cells were washed again and cell surface bound antibody was detected by flow cytometry using a Becton Dickinson FACScan. Fluorescent profiles of cells incubated with PAR antibody human AR mixtures were compared with the profiles of cells incubated with AR and a control antibody. A decrease in the level of fluorescence between cells incubated with AR and a control antibody, as compared to AR and the PAR antibodies indicated inhibition of the interaction of AR and the EGFR on the surface of A431 cells. As shown in the table depicted in FIG. 2, more than ten antibodies were tested and displayed the inhibition of AR-EGFR interaction. Also, as shown in FIG. 4, multiple PAR monoclonal antibodies were capable of neutralizing of AR-mediated activity.

Example 4

In Vitro Inhibition Assays of AR-Mediated Cell Proliferation

This example describes the antibody neutralization of amphiregulin-induced cell proliferation.

In one type of experiment mouse Balb/3T3 fibroblasts, which are capable of AR induced proliferation, were plated at $10^4$ cells/well in 96 well plates on day 0. On day 1, wells were washed and incubated in serum free medium (Life Technology) overnight. On day 2, recombinant human AR (R&D Systems) was added to the wells to at 100 ng/ml final concentration. The PAR antibodies were then added at various concentrations (0.03–10 μg/ml final concentration). On day 3, BrdU was added for 6–8 hrs, then proliferation was assessed by BrdU incorporation using a colorimetric ELISA based assay (Roche Diagnostics).

Another proliferation assay utilized HEKn (Human Epidermal Keratinocytes—neonatal) cells (Cascade Biologics). These cells proliferate to endogenously synthesized AR. HEKn cells were plated at $3\times10^3$ cells/well in 96 well black walled plates (Costar) on day 0. On day 1, wells were washed extensively with growth factor free medium (EpiLife®, a liquid growth madium) (Cascade Biologics). PAR antibodies were then added at various concentrations (0.01–3 μg/ml). After 48–72 hrs, inhibition of endogenous amphiregulin induced proliferation was assessed by quantitation of ATP using a luminescent cell viability assay (Cell-Titer-Glo®) (Promega Corp.).

Investigations were also carried our to test the in vitro inhibition of cancer cell proliferation induced by amphiregulin with anti-AR monoclonal antibodies. Various cancer cell lines (AsPC-1, PC-3, A549, HCT-116) were plated at $5\times10^3$ cells/well in 96 well plates on day 0. On day 1, wells were washed and incubated in serum free medium (Life Technology) for 8 hrs. Then wells were washed again with serum free medium and PAR antibodies were added at 10 μg/ml final concentration. After 72 hrs, inhibition of proliferation was assessed using BrdU incorporation (see above).

As shown in FIG. 2, all the listed PAR antibodies are capable of binding to AR expressed on the cell surface. These PAR antibodies showed no binding to EGF or HB EGF. Almost all the listed PAR antibodies are able to inhibit AR-mediated cell proliferation in 3T3 and HEKn cells. PAR34 and PAR80 has the most potent neutralizing capability. PAR34 can inhibit the proliferation of 3T3 cells by 50% in an amount of as little as 0.072 ug/ml, and can inhibit the proliferation of HEKn cells in an amount of as little as 0.041 ug/ml. PAR80 can inhibit the proliferation of 3T3 cells by 50% in an amount of as little as 0.072 ug/ml, and can inhibit the proliferation of HEKn cells in an amount of as little as 0.2 ug/ml. Other potent antibodies include PAR2, 5, 15, 23, 29, 31, 46, and 84. The IC50% and IC90% values of the inhibition on cell proliferation of these PAR antibodies were also listed in the table depicted in FIG. 2.

Example 5

Assay of in Vivo Efficacy of Two of the AR Neutralizing mAbs

This example describes the test in vivo efficacy of two of the AR neutralizing mAbs, PAR80 (IgG2a), and PAR34 (IgG2b) in AsPC-1 human pancreatic carcinoma and A431 epidermoid carcinoma xenograft models.

Figure 5:
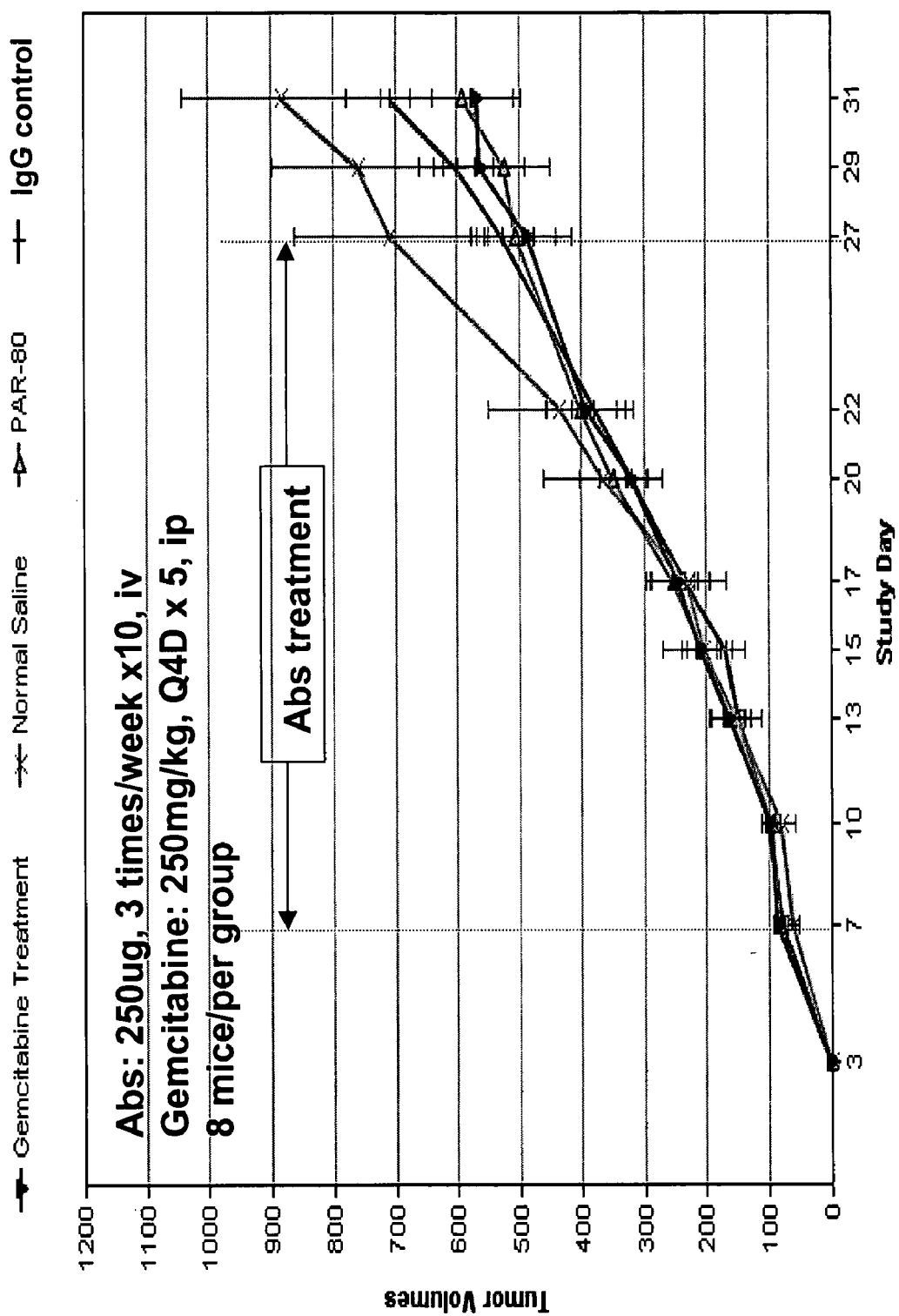
FIG. 5 depicts a plot of results of AsPC-1 in vivo treatment model study.

Treatment Model in AsPC-1 Human Pancreatic Carcinoma $10\times10^6$ AsPC-1 tumor cells were inoculated s.c. in 5 week-old, female nude mice. Mice were randomized into different treatment groups when the mean volume of tumor reached 100 mm³. A group of eight mice were treated with PAR80 antibody, first with a loading dose 500 μg/in 100 μl PBS, then with 250 μg/in 100 μl PBS, for 10 doses, 3 times/per week, via IV injection for a total dose of 3 mg/per mouse. Two control groups of eight mice each were similarly dosed with IgG or saline. Another group of eight mice were treated with gemcitabine, which is used at a dose that is considered standard chemotherapy treatment for pancreatic cancer, and thus serves as a positive control. Two weeks after the final dose, efficacy was determined by the following criteria:

The efficacy end points used for this treatment model were:
   Partial regression: tumor weight decreases to 50% of treatment start weight.
   Anti-tumor activity must be compared with the control group (statistically analyzed)
   Toxicity: Loss of 10% body weight as a general toxicity As shown in FIG. 5, treatment with PAR80 resulted in reduced tumor volume, relative to treatment with normal saline or IgG control, with no associated general toxicity based on loss of body weight (data not shown).

Prevention Model Using AsPC-1 Human Pancreatic Carcinoma and A431 Epidermoid Carcinoma Mice (n=12) were randomized into different treatment groups (12 mice per group) based on body weight. $5\times10^6$ AsPC-1 tumor cells or A431 tumor cells were inoculated s.c. in 5 week-old, female nude mice at day 0, antibody dosing started at day 1 with a first loading dose of 500 μg/100 μl PBS, then continued with 10 other doses of 250 μg/in 100 μl PBS, 3 times/per week via IV injection for a total dose of 3 mg/per mouse. Two weeks after final dose, efficacy was determined. Efficacy endpoint: anti tumor activity demonstrated by reduced size of the tumor in treated vs. control mice without associated general toxicity as defined by loss of 10% body weight.

Figure 6:
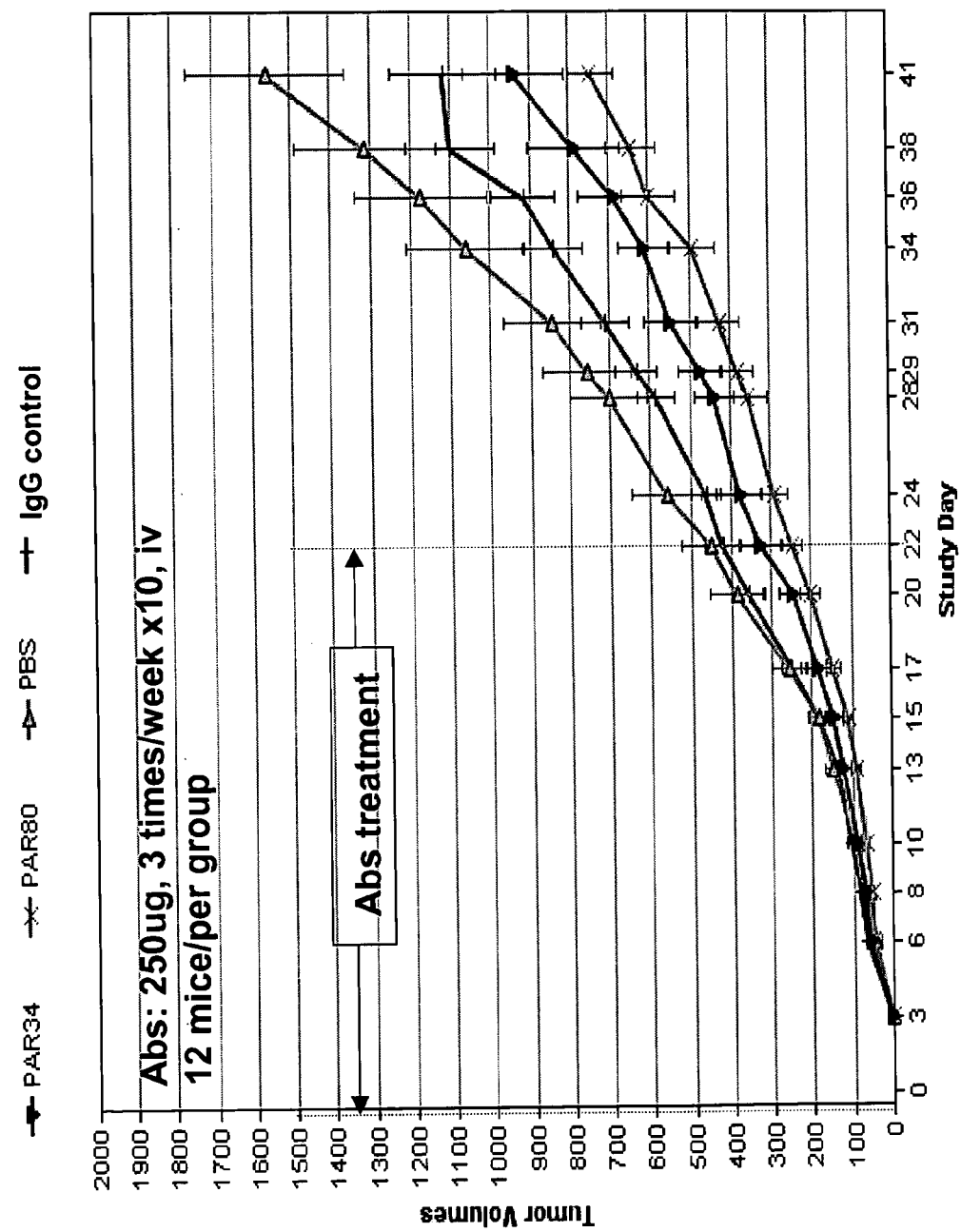
FIG. 6 depicts a plot of results of AsPC-1 in vivo prevention model study.

As shown in FIG. 6, in the AsPC-1 prevention model, both PAR34 and PAR80 demonstrated efficacy in tumor volume reduction with no associated general toxicity based on loss of body weight (data not shown).

Figure 7:
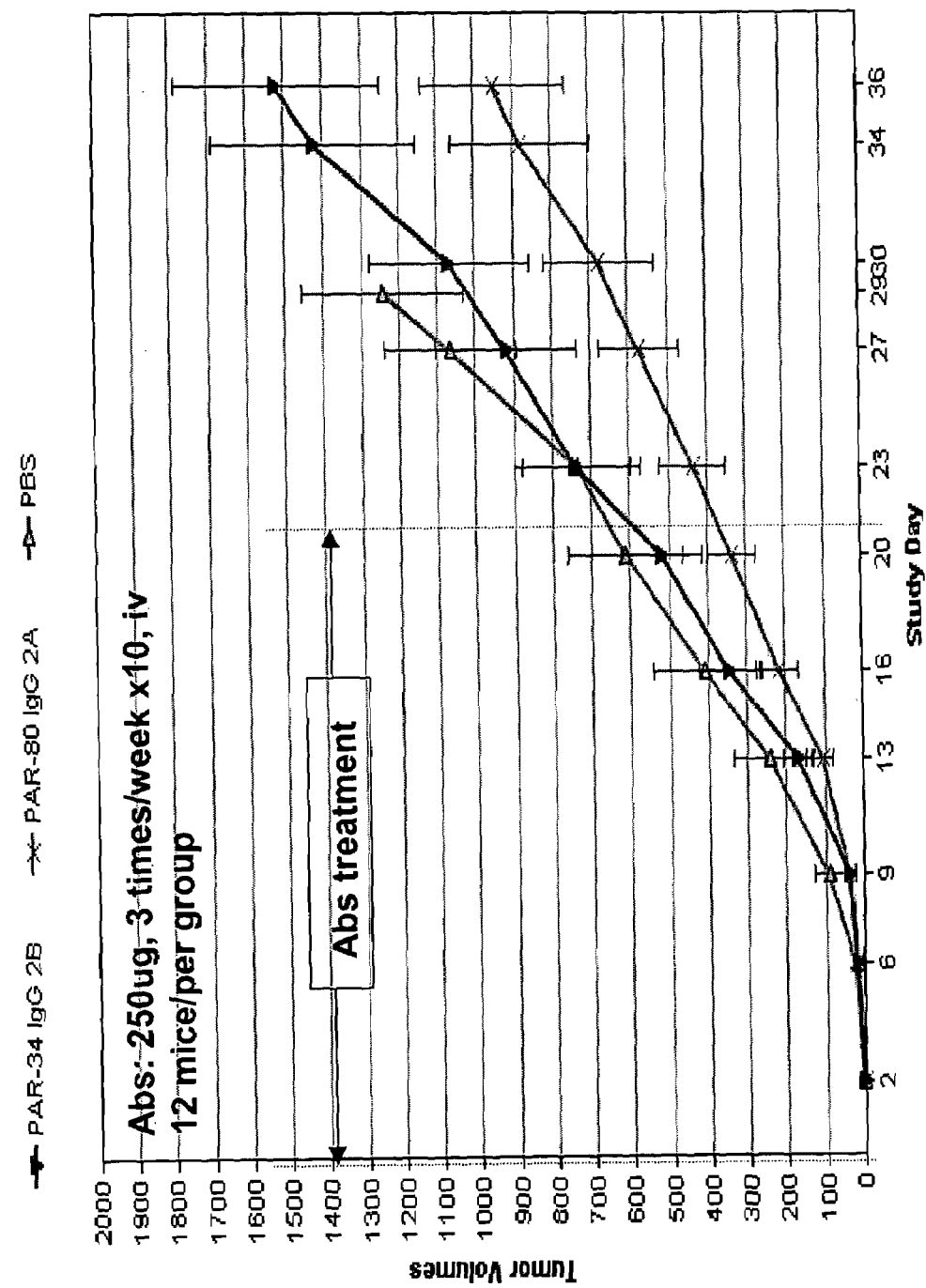
FIG. 7 depicts a plot of results of A431 in vivo prevention model study.

As shown in FIG. 7, in the A431 prevention model, PAR80 demonstrated substantial reduction in tumor volume with no associated general toxicity based on loss of body weight (data not shown).

Example 6

Humanization of an Anti-AR Antibody

This example describes the humanization of the murine anti-amphiregulin monoclonal antibody PAR34.

Humanization of PAR34 was carried out essentially according to the procedure of Queen, C. et al. (Proc. Natl. Acad. Sci. USA 86: 10029–10033 (1989)). First, human VH and VL segments with high homology to the PAR34 VH and VL amino acid sequences, respectively, were identified. Next, the CDR sequences together with framework amino acids important for maintaining the structures of the CDRs were grafted into the selected human framework sequences. In addition, human framework amino acids that were found to be rare in the corresponding V region subgroup were substituted with consensus amino acids to reduce potential immunogenicity. The resulting humanized monoclonal antibody (HuPAR34) was expressed in the mouse myeloma cell line NS0. Using a competitive binding assay with purified PAR34 and HuPAR34 antibodies, the affinity of HuPAR34 to human amphiregulin was shown to be approximately 1.8-fold lower than that of PAR34.

Cloning and Sequencing of PAR34 Variable Region cDNAs

Total RNA was extracted from approximately 107 hybridoma cells producing PAR34 using TRIzol reagent (Life Technologies, Inc., Rockville, Md.) and poly (A)$^+$ RNA was isolated with the PolyATract mRNA Isolation System (Promega Corporation, Madison, Wis.) according to the suppliers' protocols. Double-stranded cDNA was synthesized using the SMART RACE cDNA Amplification Kit (BD Biosciences Clontech, Palo Alto, Calif.) following the supplier's protocol. The variable region cDNAs for the heavy and light chains were amplified by polymerase chain reaction (PCR) using 3' primers that anneal respectively to the mouse gamma and kappa chain C regions, and a 5' universal primer provided in the SMART RACE cDNA Amplification Kit. For VH PCR, the 3' primer has the sequence 5'-GCCAGTGGATAGACTGATGG-3' (SEQ ID NO:6). For VL PCR, the 3' primer has the sequence 5'-GATGGATACAGTTGGTGCAGC-3' (SEQ ID NO:7). The VH and VL cDNAs were subcloned into the pCR4Blunt-TOPO® vector from a TOPO® cloning kit (Invitrogen Corporation, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructions.

Several heavy and light chain clones were sequenced from two independent PCR reactions. Unique sequences homologous to typical mouse heavy and light chain variable regions were identified. The cDNA sequences along with deduced amino acid sequences of the heavy and light chain V regions of PAR34 are shown in FIGS. 8 and 9, respectively.

Design of HuPAR34 Variable Regions

Humanization of the antibody variable (i.e. "V") regions was carried out as outlined by Queen, C. et al. (Proc. Natl. Acad. Sci. USA 86: 10029–10033 (1989)). First, a molecular model of the PAR34 variable regions was constructed with the aid of the computer programs ABMOD and ENCAD (Levitt, M., J. Mol. Biol. 168: 595–620 (1983)). Next, based on a homology search against human V and J segment sequences, the genomic VH segment DP-3 (Tomlinson, I. M. et al., J. Mol. Biol. 227: 776–789 (1992)) and the J segment JH4 (Ravetch, J. V. et al., Cell 27: 583–591 (1981)) were selected to provide the frameworks for the HuPAR34 heavy chain variable region. For the HuPAR34 light chain variable region, the genomic VL segment L1 (Cox, J.P. L. et al., Eur. J. Immunol. 24: 827–836 (1994)) and the J segment JK4 (Hieter, P. A. et al., J. Biol. Chem. 257: 1516–1522 (1982)) were used. The identity of the framework amino acids between PAR34 VH and the acceptor human DP-3 and JH4 segments was 68%, while the identity between PAR34 VL and the acceptor human L1 and JK4 segments was 80%.

At framework positions in which the computer model suggested significant contact with the CDRs, the amino acids from the PAR34 V regions were substituted for the original human framework amino acids. This was done at residues 28, 48, 67, 68, 70, 72, 74, and 98 of the heavy chain (FIG. 10). For the light chain, replacements were made at residues 46, 69, and 71 (FIG. 11). Framework residues that occurred only rarely at their respective positions in the corresponding human V region subgroups were replaced with human consensus amino acids at those positions. This was done at residues 17, 38 and 77 of the heavy chain (FIG. 10). The alignments of PAR34, designed HuPAR34, and the human acceptor amino acid sequences for VH and VL are shown in FIGS. 10 and 11, respectively.

Construction of HuPAR34 VH and VL Genes

A gene encoding each of HuPAR34 VH and VL was designed as a mini-exon including a signal peptide, a splice donor signal, and appropriate restriction enzyme sites for subsequent cloning into a mammalian expression vector. The splice donor signals in the VH and VL mini-exons were derived from the corresponding human germline JH and JK sequences, respectively. The signal peptide sequences in the HuPAR34 VH and VL mini-exons were derived from the corresponding PAR34 VH and VL sequences, respectively. The nucleotide sequences of HuPAR34 VH and VL genes along with deduced amino acid sequences are shown in FIGS. 12 and 13, respectively.

Figure 14:
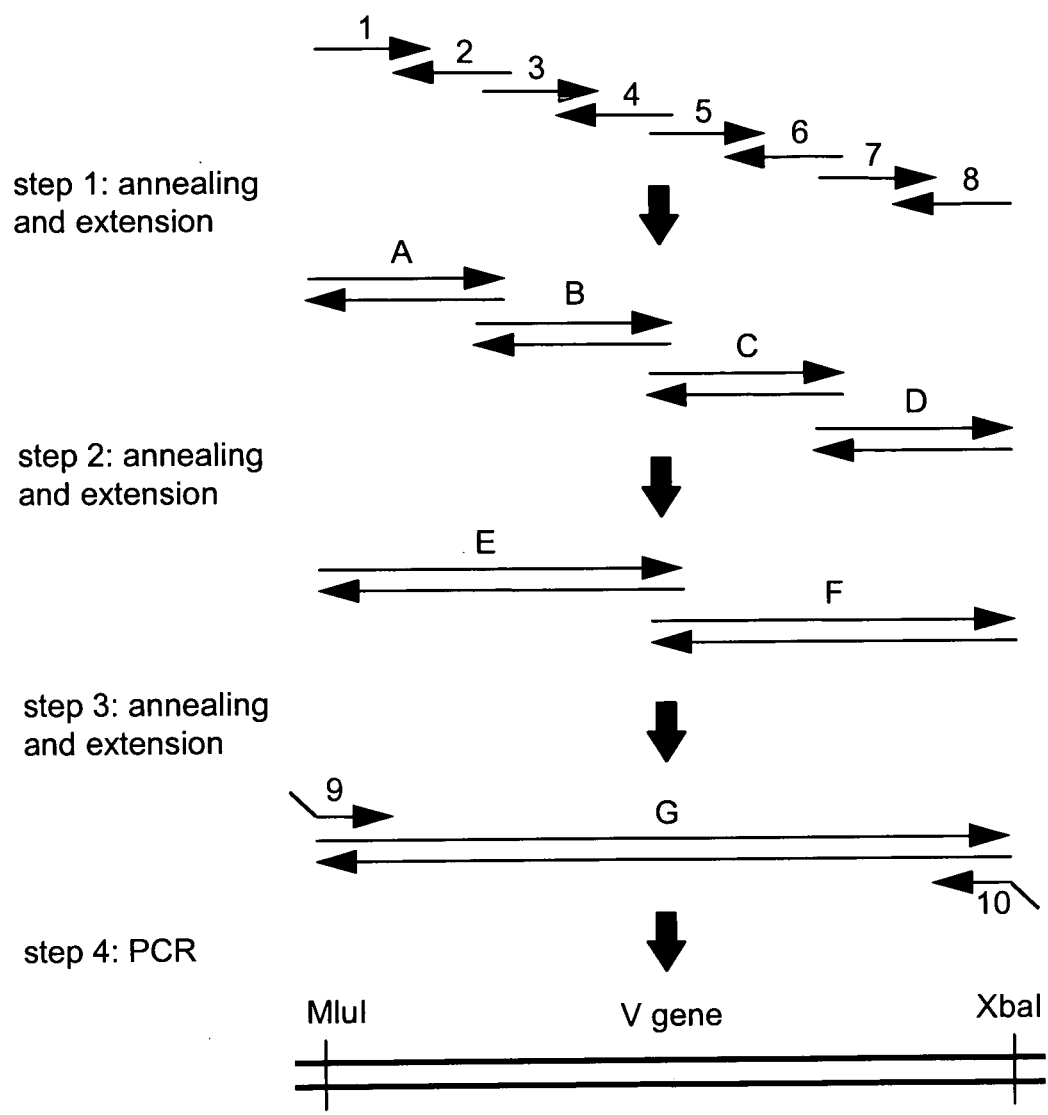
FIG. 14 depicts the scheme used for the synthesis of humanized PAR34 V genes.

The HuPAR34 VH and VL genes were constructed by extension of eight overlapping synthetic oligonucleotide primers ranging in length from approximately 60 to 80 bases and PCR amplification as illustrated in FIG. 14 (He, X.-Y. et al., J. Immunol. 160: 1029–1035 (1998)). Oligonucleotide primers 1 and 2, 3 and 4, 5 and 6, and 7 and 8 were separately annealed and extended with the Klenow fragment of DNA polymerase I. The resulting double-stranded DNA segments, A and B, and C and D, were separately mixed, denatured, annealed and extended to yield the DNA segments E and F, respectively, which were then mixed to generate the entire mini-exon (G) in the third annealing-and-extension step. The mini-exon was amplified by PCR with primers 9 and 10 using the Expand High Fidelity PCR System (Roche Diagnostics Corporation, Indianapolis, Ind.). Primers 1–10 used for the synthesis of HuPAR34 VH gene (SEQ ID NOs:20–29) and primers 1–10 used for the synthesis of VL gene (SEQ ID NOs: 30–39) are listed in FIGS. 15 and 16, respectively.

Figure 17:
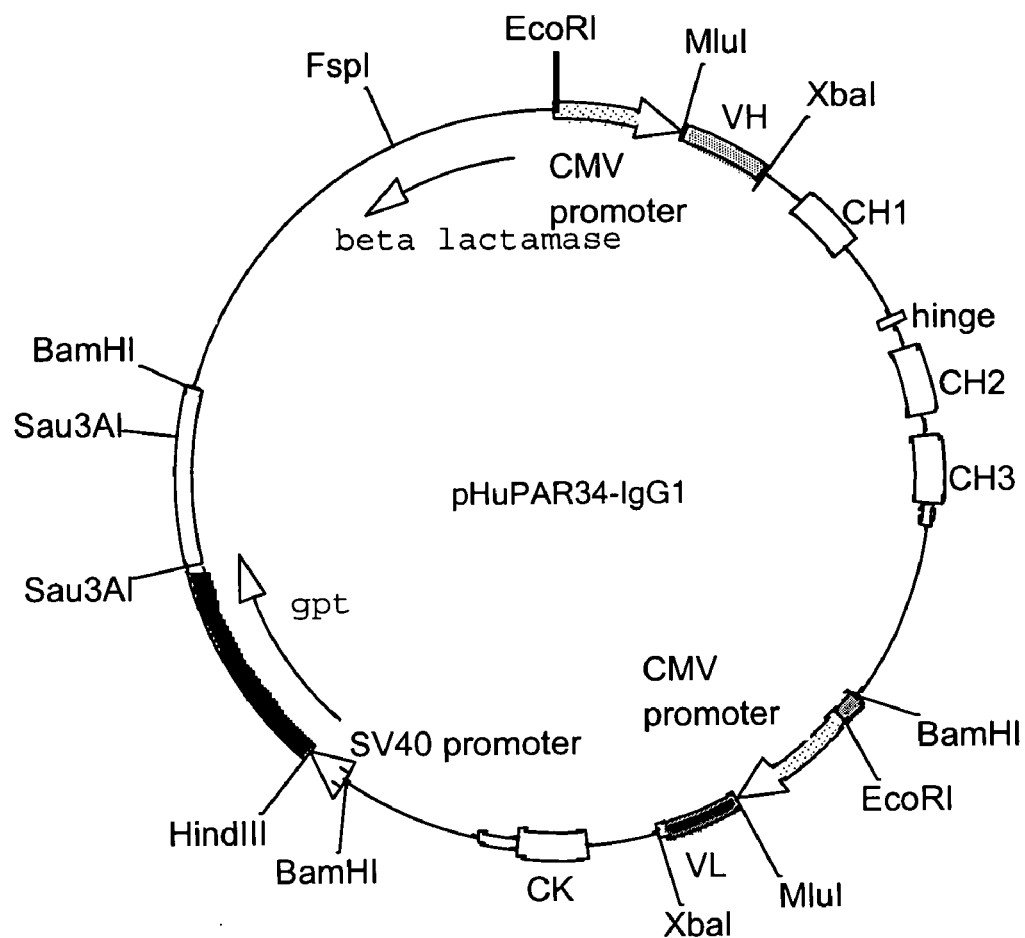
FIG. 17 depicts the structure of the vector for expression of HuPAR34 IgG1/κ.

The PCR-amplified fragments were gel-purified and digested with MluI and XbaI. The HuPAR34 VH gene was subcloned into pVg1.D.Tt, a derivative of the heavy chain expression vector pVg2.D.Tt (Cole, M. S. et al., J. Immunol. 159: 3613–3621 (1997)) in which the human γ1 gene was substituted for the human γ2 gene. The HuPAR34 VL gene was subcloned into pHuCkappa.rgpt.dE, a derivative of the kappa light chain expression vector pOKT3.Vk.rg (Cole, M. S. et al., J. Immunol. 159: 3613–3621 (1997)). After sequence confirmation, the EcoRI fragment containing the entire heavy chain transcription unit was subcloned into the unique EcoRI site in the light chain expression vector as described in Kostelny, S. A. et al. (Int. J. Cancer 93: 556–565 (2001)) to construct a single vector for expression of heavy and light chains. The resultant vector for expression of HuPAR34 in the IgG1 form, which has a structure similar to that of pHu1D10.IgG1.rgpt.dE (Kostelny, S. A. et al., Int. J. Cancer 93: 556–565 (2001)), was designated pHuPAR34-IgG1. The schematic structure of pHuPAR34-IgG1 is shown in FIG. 17.

Expression of HuPAR34

To obtain cell lines stably producing HuPAR34, the expression vector pHuPAR34-IgG 1 was introduced into the chromosome of a mouse myeloma cell line by electroporation.

Mouse myeloma cell line NS0 (European Collection of Animal Cell Cultures, Salisbury, Wiltshire, UK) was maintained in DME medium (HyClone, Logan, Utah) supplemented with 10% FBS (HyClone) and 0.1 mM non-essential amino acids (Invitrogen Corporation) at 37° C. in a 7.5% $CO_2$ incubator. Stable transfection into NSO was carried out by electroporation essentially as described in Bebbington, C. R. et al., Bio/Technology 10: 169–175 (1992). Before transfection, pHuPAR34-IgG1 was linearized using FspI. Approximately $10^7$ cells were transfected with 20 µg of linearized plasmid. The transfected cells were suspended in DME medium (HyClone) containing 10% FBS (HyClone) and 0.1 mM non-essential amino acids, and plated into several 96-well plates. After 48 hr, selection media (DME medium containing 10% FBS, 0.1 mM non-essential amino acids, HT media supplement, 0.25 mg/ml xanthine and 1 µg/ml mycophenolic acid) was applied. Approximately 10 days after the initiation of selection, culture supernatants were assayed for antibody production.

Expression of HuPAR34 was measured by sandwich ELISA. MaxiSorp ELISA plates (Nunc Nalge International, Rochester, N.Y.) were coated overnight at 4° C. with 100 µl/well of 1 µg/ml of goat anti-human IgG Fcγ-chain specific polyclonal antibodies (Jackson ImmunoResearch Laboratories, Inc., West Grove, Pa.) in 0.2 M sodium carbonate-bicarbonate buffer, pH 9.4, washed with Wash Buffer (PBS containing 0.1% Tween 20), and blocked for 15 min at room temperature with 200 µl/well of SuperBlock Blocking Buffer in TBS (Pierce Chemical Company, Rockford, IL.). After washing with Wash Buffer, samples containing HuPAR34 were appropriately diluted in ELISA Buffer (PBS containing 1% BSA and 0.1% Tween 20) and 100 µl/well was applied to the ELISA plates. As a standard, humanized anti-CD33 IgG1/κ monoclonal antibody HuM195 (Co, M. S. et al., J. Immunol., 148: 1149–1154 (1992)) was used. After incubating the plates for 1 hr at room temperature and washing with Wash Buffer, bound antibodies were detected using 100 µl/well of a 1:1000 dilution of HRP-conjugated goat anti-human kappa chain polyclonal antibodies (SouthernBiotech, Birmingham, Ala.). After incubating for 0.5 hr at room temperature and washing with Wash Buffer, color development was performed by adding 100 µl/well of ABTS substrate (KPL, Inc., Gaithersburg, Md.). Color development was stopped by adding 50 µl/well of 2% oxalic acid. Absorbance was read at 415 nm using a VersaMax microplate reader (Molecular Devices Corporation, Sunnyvale, Calif.).

One of the NS0 stable transfectants producing a high level of HuPAR34, clone v1#2, was adapted to and expanded in Protein Free Basal Medium-1 (PFBM-1) (Protein Design Labs, Inc.), expanded in PFBM-1 supplemented with Protein-Free Feed Medium-2 (PFFM-2) (Protein Design Labs, Inc.), and grown to exhaustion. After centrifugation and filtration, culture supernatant was loaded onto a protein-A Sepharose® (chromatography medium) column. The column was washed with PBS before the antibody was eluted with 0.1 M glycine-HCl (pH 2.8), 0.1 M NaCl. After neutralization with 1 M Tris-HCl (pH 8), the eluted protein was dialyzed against PBS, 0.2 µm filtered, and stored at 4° C. Antibody concentration was determined by measuring absorbance at 280 nm (1 mg/ml=1.4 $A_{280}$). Purified antibodies were characterized by SDS-PAGE analysis according to standard procedures. Analysis under non-reducing conditions indicated that HuPAR34 has a molecular weight of about 150–160 kD. Analysis under reducing conditions indicated that HuPAR34 is comprised of a heavy chain with a molecular weight of about 50 kD and a light chain with a molecular weight of about 25 kD. The purity of the antibody appeared to be more than 95%.

Binding Properties of HuPAR34

The affinity of HuPAR34 to human amphiregulin was analyzed by competition ELISA. MaxiSorp ELISA plates (Nalge Nunc International) were coated overnight at 4° C. with 100 µl/well of 0.5 µg/ml recombinant soluble human amphiregulin in 0.2 M sodium carbonate-bicarbonate buffer, pH 9.4, washed with Wash Buffer (PBS containing 0.1% Tween 20), and blocked for 15 min at room temperature with 200 µl/well of SuperBlock Blocking Buffer in TBS (Pierce Chemical Company). After washing with Wash Buffer, a mixture of biotinylated PAR34 (0.125 µg/ml final concentration) and competitor antibody (PAR34 or HuPAR34 starting at 75 µg/ml final concentration and serially diluted 3-fold) in 100 µl/well of ELISA buffer was added in triplicate. As a control, 100 µl/well of 75 µg/ml of humanized anti-CD33 IgG1/κ monoclonal antibody HuM195 (Co, M. S. et al., J. Immunol., 148: 1149–1154 (1992)) in ELISA buffer was used. As a no-competitor control, 100 µl/well of ELISA Buffer was used. After incubating the plates for 1 hr and washing with Wash Buffer, bound antibodies were detected using 100 µl/well of 1 µg/ml HRP-conjugated streptavidin (Pierce Chemical Company) in ELISA buffer. After incubating for 0.5 hr at room temperature and washing with Wash Buffer, color development was performed by adding 100 µl/well of ABTS substrate (KPL, Inc.). Color development was stopped by adding 100 µl/well of 2% oxalic acid. Absorbance was read at 415 nm.

Figure 18:
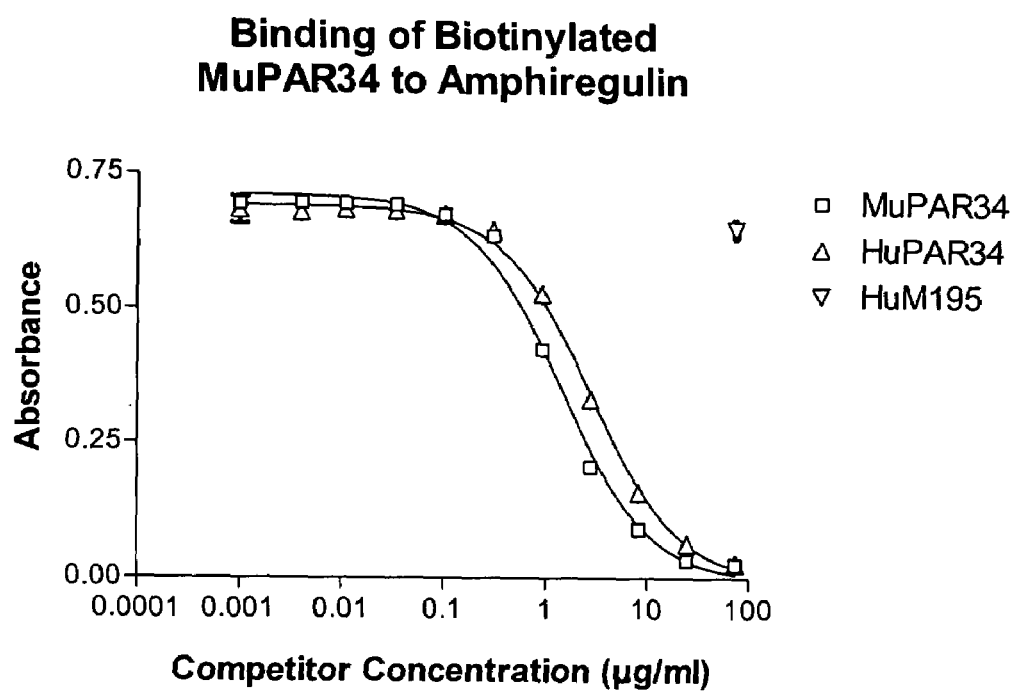
FIG. 18 depicts a plot of results from a competition ELISA measuring binding affinities of HuPAR34 and PAR34 to human amphiregulin. The binding of biotinylated PAR34 to soluble amphiregulin was analyzed in the presence of different amounts of competitor PAR34 or HuPAR34. HuM195 was used as a non-competing isotype control for HuPAR34.

A representative result of the ELISA competition experiments is shown in FIG. 18. Both PAR34 and HuPAR34 competed with biotinylated PAR34 in a concentration-dependent manner. As shown in Table 1 (below), the mean $IC_{50}$ values of PAR34 and HuPAR34, obtained using the computer software GraphPad Prism (GraphPad Software Inc., San Diego, Calif.), were 1.07 µg/ml and 1.90 µg/ml, respectively. The binding of HuPAR34 to human amphiregulin was approximately 1.8-fold less than that of PAR34. These results clearly indicate that humanization of mouse anti-amphiregulin monoclonal antibody PAR34 was successful: HuPAR34 retained binding affinity to human amphiregulin.

TABLE 1

Summary of ELISA competition experiments ($IC_{50}$)

| Competitor | Exp. A (µg/ml) | Exp. B (µg/ml) | Exp. C (µg/ml) | Exp. D (µg/ml) | Average (µg/ml) | Std. Dev. |
|---|---|---|---|---|---|---|
| PAR34 | 0.82 | 0.78 | 1.30 | 1.39 | 1.07 | 0.32 |
| HuPAR34 | 1.95 | 1.11 | 1.76 | 2.76 | 1.90 | 0.68 |
| Difference | 2.4 fold | 1.4 fold | 1.4 fold | 2.0 fold | 1.8 fold | |

Affinities between human amphiregulin (AR) and PAR34 or HuPAR34 were analyzed using BIAcore 3000 (BLAcore, Sweden).

The BIAcore analysis may be conducted according to the following protocol. PAR34 or HuPAR34 is immobilized on the Pioneer F1 chip using standard amine coupling kit (BIAcore). Surface plasmon resonance is measured at a flow rate of 50 µl/min at 24° C. Injection of AR (association phase) occurs over 180 seconds. Dissociation is subsequently monitored over 3 hours. Kinetics of binding (ka and kd) are calculated from data acquired at five different concentrations of analyte (320 nM, 160 nM, 80 nM, 40 nM, 20 nM), using the BIAevaluation program. Double-referencing is applied to eliminate responses from reference surface and buffer only control. The binding affinity, KD, is obtained by simultaneously fitting the association and dissociation phases of the sensorgram from the analyte concentration series.

Binding parameters determined using BIAcore analysis are shown below in Table 2. The BIAcore results show that HuPAR34 has an affinity for AR within 2-fold of PAR34.

TABLE 2

BIAcore analysis of antibody binding

| Antibody | $k_a$ (1/Ms) | $k_d$ (1/s) | $K_D$ (nM) |
|---|---|---|---|
| PAR34 | $4.8 \times 10^7$ | $2.4 \times 10^{-2}$ | $0.41 \pm 0.082$ |
| HuPAR34 | $1.26 \times 10^7$ | $8.23 \times 10^{-3}$ | $0.53 \pm 0.050$ |

Example 7

In Vitro Assays of HuPAR34 Inhibition of AR-Mediated Cell Proliferation

Figure 19:
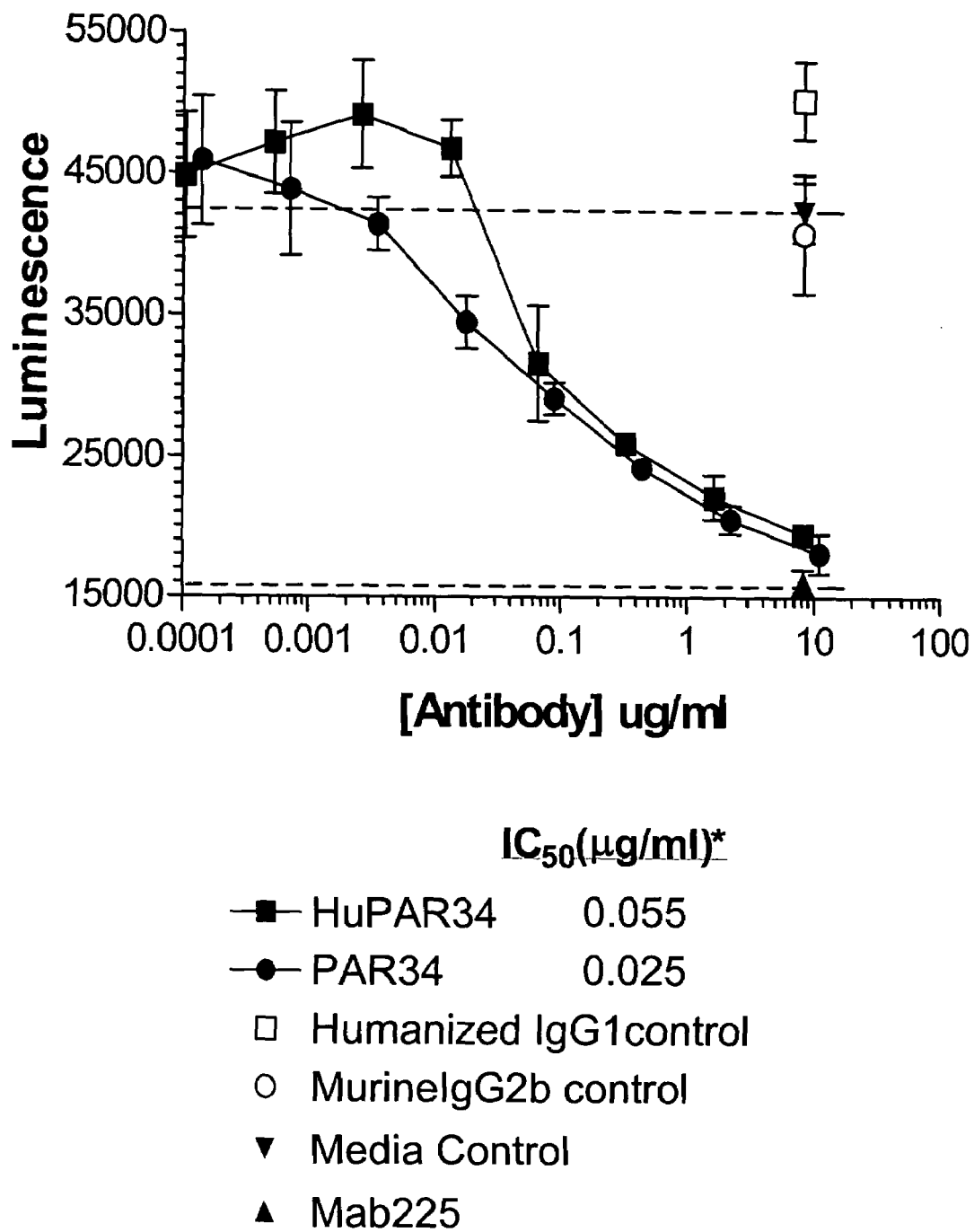
FIG. 19 depicts results of in vitro assays of HuPAR34 inhibition of AR-mediated cell proliferation.

An in vitro assay of HuPAR34 and PAR34 inhibition of AR-mediated proliferation in 3T3 cells was carried out as generally described in Example 4. Humanized IgG1 and murine IgG2b were also assayed as controls. As shown by the results depicted in FIG. 19, HuPAR34 ($IC_{50}$=0.055 µg/ml) has an antiproliferative potency within two-fold of PAR34 ($IC_{50}$=0.025 µg/ml).

Example 8

In Vivo Assay of HuPAR34 Efficacy in SCID Mouse Transplant Model

This example describes an in vivo study demonstrating the efficacy of the anti-AR antibody, HuPAR34 in the human psoriatic skin-SCID mouse transplant model (Zeigler et al., Lab Invest. 81(9):1253–61 (2001)).

Transplantation of human skin onto immunocompromised mice (either nude mice or severe-combined immunodeficient [SCID] mice) provides an approach to the study of psoriasis (Krueger, J. Invest. Dermatol. 64:307–312 (1975); Krueger et al, J. Clin. Invest. 68:1548–1557 (1981); Baker et al, Brit. J. Dermatol. 126:105–110 (1992); Nickoloff et al, Amer. J. Pathol. 146:580–588 (1995); Wrone-Smith and Nickoloff, J. Clin. Invest. 98:1878–1887 (1996); Ellis et al., Arch. Dermatology. 136:609–616 (1999)). Using this approach, it has been shown that phenotypic features of the disease (i.e., epidermal thickening, extensive rete peg formation and presence of inflammatory cells) are maintained for an extended period in the transplanted skin (Nickoloff et al, Amer. J. Pathol. 146:580–588 (1995)).

Two human donors of psoriatic skin and two donors of normal skin were recruited for the study. Tissue was transplanted to eight SCID mice (CB-17 strain; Taconic Farms Inc., Germantown, N.Y.), four receiving normal skin transplants and four receiving psoriatic skin transplants. Normal human skin and psoriatic lesional plaque skin were transplanted onto the dorsal surface of recipient SCID mice and the mice treated generally following the procedure described in Zeigler et al., Lab Invest. 81(9):1253–61 (2001). Briefly, one punch biopsied tissue sample was transplanted onto mouse as follows. After mice were anesthetized by intraperitoneal injection of sodium pentobarbital (Butler Co., Columbus, Ohio, at a dose of 1.8 mg in 0.2 ml per 25 gm mouse), the dorsal region of each mouse was shaved. Mouse skin was surgically removed to size and replaced with the human tissue. This tissue was secured to the back of the mice with absorbable sutures (4-0 Dexon "S", Davis-Geck, Manati, Puerto Rico). The transplants were then bandaged with Xeroform petrolatum dressing (Kendall Company; Mansfield, Mass.) for 5 days. The animals were maintained in a pathogen-free environment throughout the preparation and treatment phases. The skin grafts were allowed to heal for 1–2 weeks prior to the initiation of treatment. Transplanted animals were randomly assigned to one of two treatment groups.

After allowing the tissue to heal HuPAR34 and IgG2b control antibody were tested for treatment on the SCID mice. The identity of the antibodies remained blinded during the duration of the study. The treatment protocol consisted of intraperitoneal injection of 200 µl of a 1 mg/ml solution of the antibody per animal every three days for 24 days for a total of eight doses (21 day treatment period). Mice were weighed on the first and last day of antibody treatment. At the end of the treatment period, the mice were sacrificed, and the transplanted human tissue (and a small amount of surrounding mouse skin) was surgically removed and fixed in 10% buffered formalin.

After embedding tissue in paraffin, multiple 5-micron sections were cut from each tissue piece, mounted onto microscope slides and stained with hematoxylin and eosin. Epidermal area was measured as a function of changes in epidermal thickness per unit length using NIH Image analysis software. Specifically, tissue sections were visualized by light microscopy at 10× magnification. At this level of magnification the entire epidermal area of each tissue section is "captured" in equal segments (normally 3–4 segments across a typical tissue section) and the area of each segment was quantified using the NIH Image analysis program. Multiple areas from each transplant was quantified in this way to provide high n values. From these values, mean epidermal area was determined. Prior to transplantation, a small piece of tissue from each donor was fixed in 10% buffered formalin and used for zero-time assessment of epidermal thickness.

In addition to quantitative evaluation, skin grafts were also evaluated histologically. Characteristics of psoriasis including epidermal hyperplasia, increased rete peg formation and dermal and/or intra-epidermal infiltration with lymphocytes, macrophages and neutrophils were obtained.

Results

Table 3 provides quantitative data from the study.

TABLE 3

Epidermal thickness of normal human skin and psoriatic human skin before and after SCID mouse transplantation and treatment.

| Group | Epidermal thickness (µm²)[1] |
|---|---|
| Normal skin (pre-transplantation) | 31.0 ± 11.5 (n = 24) |
| Normal skin (post-transplant) + Reagent A (Ig2b) | 158.5 ± 35.5 (n = 79) |
| Normal skin (post-transplant) + Reagent B (HuPAR34) | 53.0 ± 12.0 (n = 110) |
| Psoriatic skin – pre-transplantation. | 178.5 ± 40.5 (n = 28) |
| Psoriatic skin – post-transplant + Reagent A (Ig2b) | 104.5 ± 44.0 (n = 106) |
| Psoriatic skin – post-transplant + Reagent B (HuPAR34) | 46.5 ± 16.5 (n = 172) |

[1]Values shown are means and standard deviations based on multiple areas in multiple histological sections per mouse transplanted with skin samples from four normal and four psoriatic donors.

Normal skin was much thinner than psoriatic plaque skin immediately upon biopsy, although consistent with previous skin transplant studies (see e.g., Ellis et al, 2000; Zeigler et al, 2001), the normal skin did undergo a hyperproliferative response after transplantation.

The psoriatic skin maintained a hyperproliferative phenotype through the period following transplantation and during treatment.

Most significantly, HuPAR34 (reagent B), but not Ig2b control (reagent A), dramatically suppressed the hyperproliferative conditions in both the transplanted normal skin and the transplanted psoriatic plaque skin. FIGS. 20C and 20D show light microscopy images of tissue sections of transplanted normal skin after treatment with Ig2b (FIG. 20C) or HuPAR34 (FIG. 20D). FIGS. 21A and 21B show light microscopy images of tissue sections of transplanted psoriatic skin after treatment with Ig2b (FIG. 21A) or HuPAR34 (FIG. 21B).

Figure 20:
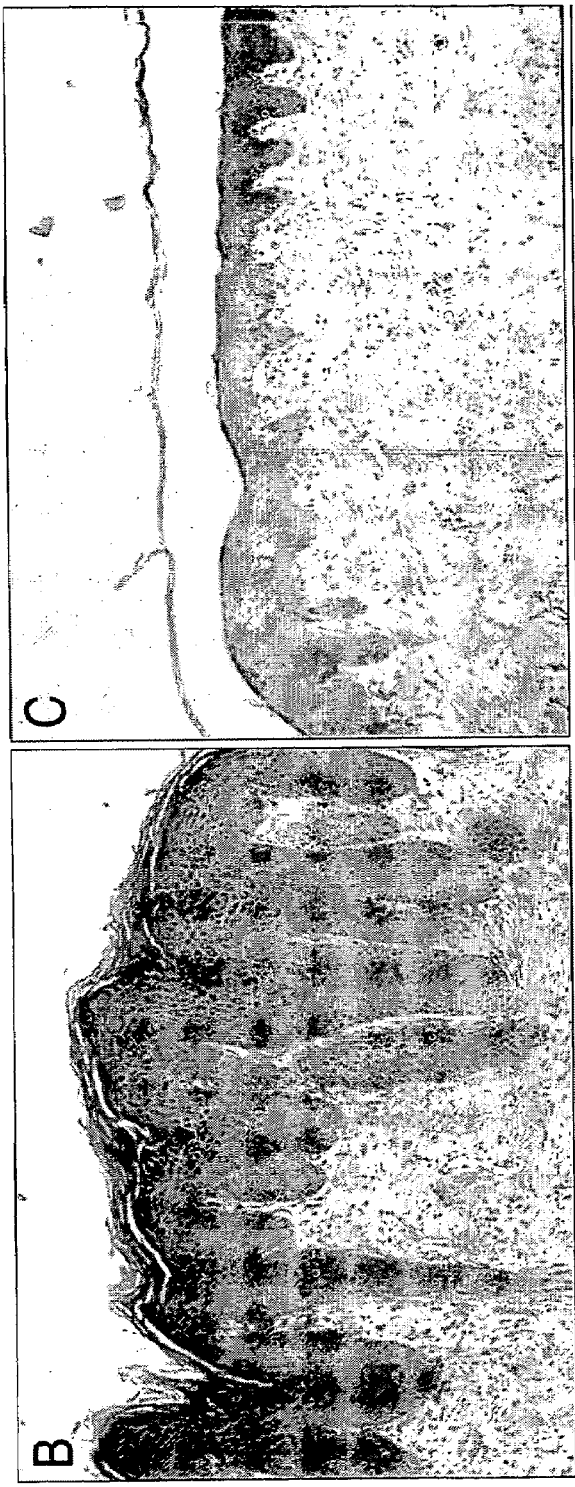
FIG. 20 depicts light microscopy images of tissue sections of transplanted normal skin after treatment with: (C) Ig2b; or (D) HuPAR34.
Figure 21:
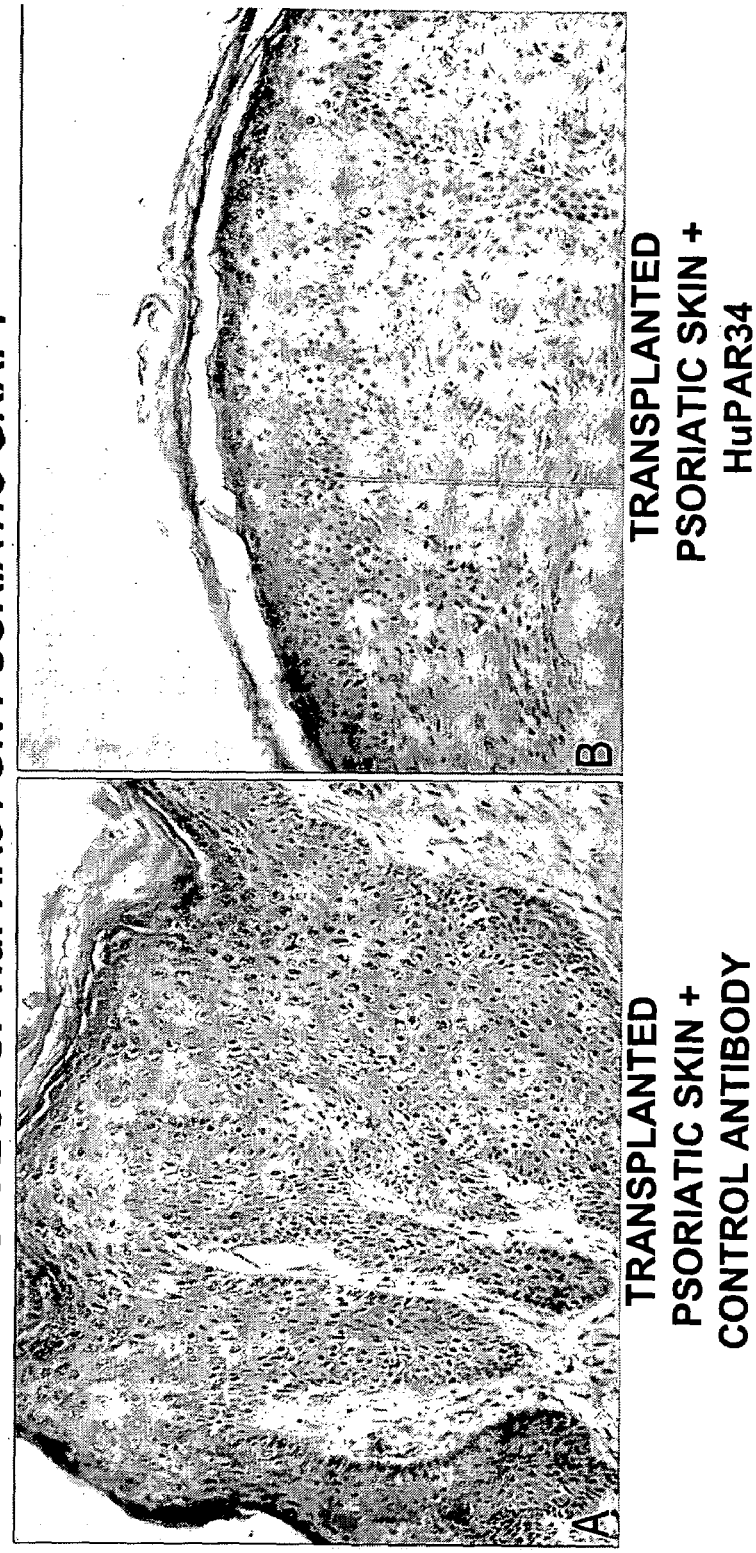
FIG. 21 light microscopy images of tissue sections of transplanted psoriatic skin after treatment with: (A) Ig2b; or (B) HuPAR34.

As demonstrated by the images in FIGS. 20 and 21, HuPAR34 dramatically suppresses keratinocyte proliferation in both normal and psoriatic skin grafts when compared to treatment with a control antibody.

Example 9

In Vitro Assay of the Effect of HuPAR34 on Human Epidermal Keratinocytes and Dermal Fibroblasts in Monolayer Culture Based on the results of Example 8 described above, where treatment with HuPAR34, but not Ig2b control, significantly reduced epidermal thickness, it was proposed to assess the effects of the same two reagents on proliferation of keratinocytes in monolayer culture.

Normal human epidermal keratinocytes and human dermal fibroblasts were isolated from human skin as described previously (Varani et al, Arch Dermatol Res. 286:443–7 (1994)). Using standard in vitro assay procedures, we assessed the effects of reagents A (Ig2b) and B (HuPAR34) on proliferation of both cell types and synthesis of type I procollagen in the dermal fibroblast population. The in vitro assays were carried out as described in a recent report (Bhagavathula et al, J Invest Dermatol 122: 130–139 (2004)).

Results

Figure 22:
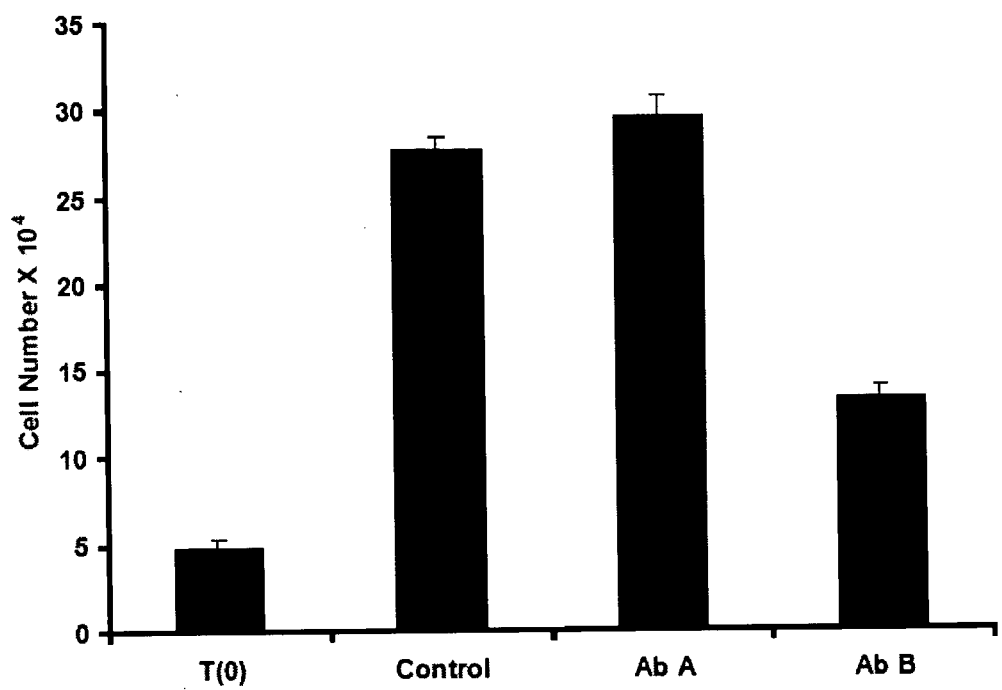
FIG. 22 depicts results of in vitro growth assays of the effect of HuPAR34 or Ig2b on human epidermal keratinocytes.

As shown by the chart depicted in FIG. 22, there was a significant reduction in proliferation of keratinocytes with HuPAR34 ("Ab B"), while no reduction was observed with the IgG2b control antibody ("Ab A").

In parallel studies, the same two antibodies, HuPAR34 and Ig2b, were assayed for their effect on human dermal fibroblast proliferation. As shown by the top chart depicted in FIG. 23, neither Ig2b ("Ab A") or HuPAR34 ("Ab B") affected dermal fibroblast proliferation. Likewise, as shown in the bottom chart depicted in FIG. 23, neither Ig2b or HuPAR34 affected the elaboration of type I procollagen by human dermal fibroblasts.

Taken together, the results described in Examples 8 and 9 demonstrate that intraperitoneal injection of HuPAR34 into SCID mice with human skin transplants was effective in suppressing epidermal hyperplasia in the human skin. This was observed in psoriatic plaque skin, which was hyperplastic prior to transplantation, as well as in normal skin, which becomes hyperplastic as a function of transplantation and maintenance on the SCID mouse. The fact that Ig2b did not suppress proliferation of epidermal keratinocytes suggests specificity associated with the response to HuPAR34.

In contrast to HuPAR34, two different agents believed to affect T-lymphocyte function, cyclosporin A and antibody to CD11b, reduce the hyperplastic response associated with psoriasis but did not inhibit hyperplasia of transplanted normal skin.

Agents with broader specificity (e.g. synthetic corticosteroid and a PPAR-γ ligands), on the other hand, appear to suppress proliferation of psoriatic skin but concomitantly suppress epidermal proliferation in transplanted normal skin (Ellis et al, Arch. Dermatology. 136:609–616 (2000); Zeigler et al, Lab. Invest. 81:1253–1261, (2001)). One interpretation of these findings is that the agents which targeted only psoriatic skin probably did so by acting on the immune basis of the disease, while the broad specificity agents such as corticosteroid and Troglitazone (a PPAR-γ ligand) likely affect down-stream events in the keratinocyte autocrine proliferation pathway.

In spite of its ability to suppress the epidermal hyperplastic response in transplanted normal skin and its ability to suppress autocrine keratinocyte growth in monolayer culture, HuPAR34 does not appear affect fibroblast function when used at doses that suppress epidermal proliferation. In this respect, the mechanism of action of HuPAR34 appears to differ significantly from corticosteroids since the potent steroids suppress both epidermal and dermal function. The ability of HuPAR34 to effectively suppress epidermal hyperplasia without a detrimental effect on dermal fibroblast function makes HuPAR34 a useful agent for treating various hyperproliferative conditions including psoriasis.

Although the invention has been described with reference to the presently preferred embodiments, it should be understood that various modifications may be made without departing from the spirit of the invention.

All publications, patents, patent applications, and web sites are herein incorporated by reference in their entirety to the same extent as if each individual patent, patent application, or web site was specifically and individually indicated to be incorporated by reference in its entirety.

What is claimed is:

1. A chimeric, humanized or human antibody that specifically binds to amphiregulin (AR) comprising a heavy chain variable region defined by SEQ ID NO: 2 and a light chain variable region defined by SEQ ID NO: 3.

2. A chimeric, humanized or human antibody that specifically binds to amphiregulin (AR) comprising a heavy chain variable region defined by SEQ ID NO: 4 and a light chain variable region defined by SEQ ID NO: 5.

3. A chimeric, humanized or human antibody that specifically binds to amphiregulin (AR) comprising a heavy chain variable region defined by SEQ ID NO: 12 and a light chain variable region defined by SEQ ID NO: 14.

4. The antibody of claim 3, wherein the antibody is an antigen binding fragment that is selected from the group consisting of Fab, Fab', F(ab')$_2$, Fv fragments, rIgG, diabodies, single chain antibodies, and multispecific antibodies.

5. The antibody of claim 3, wherein the antibody is conjugated to an effector moiety.

6. A pharmaceutical composition comprising the antibody of claim 3 and a pharmaceutically acceptable excipient.

* * * * *

SEQUENCE LISTING

<160> NUMBER OF SEQ ID NOS: 39

<210> SEQ ID NO 1
<211> LENGTH: 252
<212> TYPE: PRT
<213> ORGANISM: homo sapiens

<400> SEQUENCE: 1

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

```
Phe Glu Val Thr Ser Arg Ser Glu Met Ser Ser Gly Ser Glu Ile Ser
 50                  55                  60
Pro Val Ser Glu Met Pro Ser Ser Glu Pro Ser Ser Gly Ala Asp
 65                  70                  75                  80
Tyr Asp Tyr Ser Glu Glu Tyr Asp Asn Glu Pro Gln Ile Pro Gly Tyr
                 85                  90                  95
Ile Val Asp Asp Ser Val Arg Val Glu Gln Val Val Lys Pro Pro Gln
                 100                 105                 110
Asn Lys Thr Glu Ser Glu Asn Thr Ser Asp Lys Pro Lys Arg Lys Lys
                 115                 120                 125
Lys Gly Gly Lys Asn Gly Lys Asn Arg Arg Asn Arg Lys Lys Lys Asn
 130                 135                 140
Pro Cys Asn Ala Glu Phe Gln Asn Phe Cys Ile His Gly Glu Cys Lys
145                  150                 155                 160
Tyr Ile Glu His Leu Glu Ala Val Thr Cys Lys Cys Gln Gln Glu Tyr
                 165                 170                 175
Phe Gly Glu Arg Cys Gly Glu Lys Ser Met Lys Thr His Ser Met Ile
                 180                 185                 190
Asp Ser Ser Leu Ser Lys Ile Ala Leu Ala Ala Ile Ala Ala Phe Met
                 195                 200                 205
Ser Ala Val Ile Leu Thr Ala Val Ala Val Ile Thr Val Gln Leu Arg
 210                 215                 220
Arg Gln Tyr Val Arg Lys Tyr Glu Gly Glu Ala Glu Glu Arg Lys Lys
225                  230                 235                 240
Leu Arg Gln Glu Asn Gly Asn Val His Ala Ile Ala
                 245                 250

<210> SEQ ID NO 2
<211> LENGTH: 119
<212> TYPE: PRT
<213> ORGANISM: mus sp.

<400> SEQUENCE: 2

Glu Ile Gln Leu Gln Gln Ser Gly Pro Glu Leu Val Lys Pro Gly Ala
 1               5                  10                  15
Ser Val Lys Val Ser Cys Lys Ala Ser Gly Tyr Ala Phe Thr Asn Tyr
                 20                  25                  30
Asn Met Tyr Trp Val Lys Gln Ser His Gly Lys Ser Leu Glu Trp Ile
                 35                  40                  45
Gly Tyr Ile Asp Pro Tyr Tyr Gly Asp Pro Gly Tyr Ser Gln Lys Phe
 50                  55                  60
Lys Gly Lys Ala Thr Leu Thr Val Asp Lys Ser Ser Ser Thr Ala Tyr
 65                  70                  75                  80
Met His Leu Asn Ser Leu Thr Ser Glu Asp Ser Ala Val Tyr Tyr Cys
                 85                  90                  95
Ala Arg Arg Gly Asn Phe Pro Tyr Tyr Phe Asp Tyr Trp Gly Gln Gly
                 100                 105                 110
Thr Thr Leu Thr Val Ser Ser
         115

<210> SEQ ID NO 3
<211> LENGTH: 107
<212> TYPE: PRT
<213> ORGANISM: mus sp.

<400> SEQUENCE: 3
```

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
                100                 105

<210> SEQ ID NO 4
<211> LENGTH: 116
<212> TYPE: PRT
<213> ORGANISM: mus sp.

<400> SEQUENCE: 4

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Cys Ile Asp Pro Glu Asn Gly Asp Thr Glu Tyr Ala Pro Asn Phe
    50                  55                  60

Gln Gly Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Tyr Gly Gly Thr Ile Thr Phe Ala Tyr Trp Gly Gln Gly Thr Leu Val
                100                 105                 110

Thr Val Ser Ala
        115

<210> SEQ ID NO 5
<211> LENGTH: 110
<212> TYPE: PRT
<213> ORGANISM: mus sp.

<400> SEQUENCE: 5

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Ser Ala Asn Trp Val Gln Glu Lys Pro Asp His Leu Phe Thr Gly
        35                  40                  45

Leu Ile Gly Gly Thr Ile Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95
```

His Trp Val Phe Gly Gly Gly Thr Lys Leu Thr Val Leu Gly
            100                 105                 110

<210> SEQ ID NO 6
<211> LENGTH: 20
<212> TYPE: DNA
<213> ORGANISM: Artificial
<220> FEATURE:
<223> OTHER INFORMATION: Oligonucleotide

<400> SEQUENCE: 6
gccagtggat agactgatgg                                           20

<210> SEQ ID NO 7
<211> LENGTH: 21
<212> TYPE: DNA
<213> ORGANISM: Artificial
<220> FEATURE:
<223> OTHER INFORMATION: Oligonucleotide

<400> SEQUENCE: 7
gatggataca gttggtgcag c                                         21

<210> SEQ ID NO 8
<211> LENGTH: 414
<212> TYPE: DNA
<213> ORGANISM: mus sp.

<400> SEQUENCE: 8
atggaatgga gatggatctt tctcttcctc ctgtcaggaa ctacaggtgt ccactctgag    60
atccagctgc agcagtctgg acctgagctg gtgaagcctg gggcttcagt gaaggtatcc   120
tgcaaggctt ctggttatgc attcactaac tacaacatgt actgggtgaa gcagagccat   180
ggaaagagcc ttgagtggat tggatatatt gatccttact atggtgatcc tggctacagc   240
cagaagttca aggcaaggc cacattgact gttgacaagt cctccagcac agcctacatg   300
catctcaaca gcctgacatc tgaggactct gcagtctatt actgtgcaag acggggtaac   360
ttcccgtact actttgacta ctggggccaa ggcaccactc tcacagtctc ctca         414

<210> SEQ ID NO 9
<211> LENGTH: 138
<212> TYPE: PRT
<213> ORGANISM: mus sp.

<400> SEQUENCE: 9

Met Glu Trp Arg Trp Ile Phe Leu Phe Leu Leu Ser Gly Thr Thr Gly
1               5                   10                  15

Val His Ser Glu Ile Gln Leu Gln Gln Ser Gly Pro Glu Leu Val Lys
            20                  25                  30

Pro Gly Ala Ser Val Lys Val Ser Cys Lys Ala Ser Gly Tyr Ala Phe
        35                  40                  45

Thr Asn Tyr Asn Met Tyr Trp Val Lys Gln Ser His Gly Lys Ser Leu
    50                  55                  60

Glu Trp Ile Gly Tyr Ile Asp Pro Tyr Tyr Gly Asp Pro Gly Tyr Ser
65                  70                  75                  80

Gln Lys Phe Lys Gly Lys Ala Thr Leu Thr Val Asp Lys Ser Ser Ser
                85                  90                  95

Thr Ala Tyr Met His Leu Asn Ser Leu Thr Ser Glu Asp Ser Ala Val
            100                 105                 110

Tyr Tyr Cys Ala Arg Arg Gly Asn Phe Pro Tyr Tyr Phe Asp Tyr Trp

```
              115                 120                 125
Gly Gln Gly Thr Thr Leu Thr Val Ser Ser
        130                 135

<210> SEQ ID NO 10
<211> LENGTH: 381
<212> TYPE: DNA
<213> ORGANISM: mus sp.

<400> SEQUENCE: 10
atgaggaccc ctgctcagtt tcttggaatc ttgttgctct ggtttccagg tatcaaatgt    60
gacatcaaga tgacccagtc tccatcttcc atgtatgcat ctctaggaga gagagtcact   120
atcacttgca aggcgagtca ggacattaat agctatttaa gctggttcca gcagaaacca   180
gggaaatctc ctaagaccct gatctatcgt gcaaacagat tggtagatgg ggtcccatca   240
aggttcagtg gcagtggatc tgggcaagat tattctctca ccatcagcag cctggagtat   300
gaagatatgg gaatttatta ttgtctacag tatgatgagt ttccgtacac gttcggaggg   360
gggaccaagc tggaaataaa a                                             381

<210> SEQ ID NO 11
<211> LENGTH: 127
<212> TYPE: PRT
<213> ORGANISM: mus sp.

<400> SEQUENCE: 11

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Asn Ser Tyr Leu Ser Trp Phe Gln Gln Lys Pro Gly Lys Ser Pro
    50                  55                  60

Lys Thr Leu Ile Tyr Arg Ala Asn Arg Leu Val Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Ile Tyr Tyr Cys Leu Gln Tyr Asp
            100                 105                 110

Glu Phe Pro Tyr Thr Phe Gly Gly Gly Thr Lys Leu Glu Ile Lys
        115                 120                 125

<210> SEQ ID NO 12
<211> LENGTH: 119
<212> TYPE: PRT
<213> ORGANISM: Artificial
<220> FEATURE:
<223> OTHER INFORMATION: Humanized antibody

<400> SEQUENCE: 12

Glu Val Gln Leu Val Gln Ser Gly Ala Glu Val Lys Lys Pro Gly Ala
1               5                   10                  15

Ser Val Lys Ile Ser Cys Lys Val Ser Gly Tyr Ala Phe Thr Asn Tyr
            20                  25                  30

Asn Met Tyr Trp Val Arg Gln Ala Pro Gly Lys Gly Leu Glu Trp Ile
        35                  40                  45

Gly Tyr Ile Asp Pro Tyr Tyr Gly Asp Pro Gly Tyr Ser Gln Lys Phe
```

```
                       50                  55                  60
Lys Gly Lys Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Arg Gly Asn Phe Pro Tyr Tyr Phe Asp Tyr Trp Gly Gln Gly
                    100                 105                 110

Thr Leu Val Thr Val Ser Ser
                    115

<210> SEQ ID NO 13
<211> LENGTH: 119
<212> TYPE: PRT
<213> ORGANISM: homo sapiens
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(66)
<223> OTHER INFORMATION: Xaa can be any naturally occurring amino acid
<220> FEATURE:
<221> NAME/KEY: misc_feature
<222> LOCATION: (99)..(108)
<223> OTHER INFORMATION: Xaa can be any naturally occurring amino acid

<400> SEQUENCE: 13

Glu Val Gln Leu Val Gln Ser Gly Ala Glu Val Lys Lys Pro Gly Ala
  1               5                  10                  15

Thr Val Lys Ile Ser Cys Lys Val Ser Gly Tyr Thr Phe Thr Xaa Xaa
                 20                  25                  30

Xaa Xaa Xaa Trp Val Gln Gln Ala Pro Gly Lys Gly Leu Glu Trp Met
             35                  40                  45

Gly Xaa Xaa Xaa Xaa Xaa Xaa Xaa Xaa Xaa Xaa Xaa Xaa Xaa Xaa Xaa
 50                  55                  60

Xaa Xaa Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                     85                  90                  95

Ala Thr Xaa Xaa Xaa Xaa Xaa Xaa Xaa Xaa Xaa Xaa Trp Gly Gln Gly
                    100                 105                 110

Thr Leu Val Thr Val Ser Ser
                    115

<210> SEQ ID NO 14
<211> LENGTH: 107
<212> TYPE: PRT
<213> ORGANISM: Artificial
<220> FEATURE:
<223> OTHER INFORMATION: Humanized antibody

<400> SEQUENCE: 14

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Ile Asn Ser Tyr
                 20                  25                  30

Leu Ser Trp Phe Gln Gln Lys Pro Gly Lys Ala Pro Lys Thr Leu Ile
             35                  40                  45

Tyr Arg Ala Asn Arg Leu Val Asp Gly Val Pro Ser Arg Phe Ser Gly
 50                  55                  60
```

```
Ser Gly Ser Gly Gln Asp Tyr Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                 85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: homo sapiens
<220> FEATURE:
<221> NAME/KEY: misc_feature
<222> LOCATION: (24)..(34)
<223> OTHER INFORMATION: Xaa can be any naturally occurring amino acid
<220> FEATURE:
<221> NAME/KEY: misc_feature
<222> LOCATION: (50)..(56)
<223> OTHER INFORMATION: Xaa can be any naturally occurring amino acid
<220> FEATURE:
<221> NAME/KEY: misc_feature
<222> LOCATION: (89)..(97)
<223> OTHER INFORMATION: Xaa can be any naturally occurring amino acid

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys Xaa Xaa Xaa Xaa Xaa Xaa Xaa Xaa
                 20                  25                  30

Xaa Xaa Trp Phe Gln Gln Lys Pro Gly Lys Ala Pro Lys Ser Leu Ile
         35                  40                  45

Tyr Xaa Xaa Xaa Xaa Xaa Xaa Xaa Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Xaa Xaa Xaa Xaa Xaa Xaa Xaa
                 85                  90                  95

Xaa Phe Gly Gly Gly Thr Lys Val Glu Ile Lys
            100                 105

<210> SEQ ID NO 16
<211> LENGTH: 448
<212> TYPE: DNA
<213> ORGANISM: Artificial
<220> FEATURE:
<223> OTHER INFORMATION: Humanized antibody

<400> SEQUENCE: 16
acgcgtccac catggaatgg agatggatct ttctcttcct cctgtcagga actacaggtg      60
tccactctga ggtccagctg gtgcagtctg gagctgaggt gaagaagcct ggggcttctg     120
tgaaaatatc ctgcaaggtt tctggttatg cattcactaa ctacaacatg tattgggtga     180
ggcaggcccc tggaaagggc cttgagtgga ttggatatat tgatccttac tatggtgatc     240
ctggctacag ccagaagttc aagggcaagg ccacattgac tgttgacaag tccaccagca     300
cagcctacat ggagctcagc agcctgaggt ctgaggacac tgcagtctat tactgtgcaa     360
gacgtggcaa cttcccgtac tactttgact actggggcca aggcaccctt gtcacagtct     420
catcaggtga gtcctcacaa cctctaga                                        448

<210> SEQ ID NO 17
```

<211> LENGTH: 138
<212> TYPE: PRT
<213> ORGANISM: Artificial
<220> FEATURE:
<223> OTHER INFORMATION: Humanized antibody

<400> SEQUENCE: 17

Met Glu Trp Arg Trp Ile Phe Leu Phe Leu Leu Ser Gly Thr Thr Gly
1               5                   10                  15

Val His Ser Glu Val Gln Leu Val Gln Ser Gly Ala Glu Val Lys Lys
            20                  25                  30

Pro Gly Ala Ser Val Lys Ile Ser Cys Lys Val Ser Gly Tyr Ala Phe
        35                  40                  45

Thr Asn Tyr Asn Met Tyr Trp Val Arg Gln Ala Pro Gly Lys Gly Leu
    50                  55                  60

Glu Trp Ile Gly Tyr Ile Asp Pro Tyr Tyr Gly Asp Pro Gly Tyr Ser
65                  70                  75                  80

Gln Lys Phe Lys Gly Lys Ala Thr Leu Thr Val Asp Lys Ser Thr Ser
            85                  90                  95

Thr Ala Tyr Met Glu Leu Ser Ser Leu Arg Ser Glu Asp Thr Ala Val
        100                 105                 110

Tyr Tyr Cys Ala Arg Arg Gly Asn Phe Pro Tyr Tyr Phe Asp Tyr Trp
    115                 120                 125

Gly Gln Gly Thr Leu Val Thr Val Ser Ser
130                 135

<210> SEQ ID NO 18
<211> LENGTH: 415
<212> TYPE: DNA
<213> ORGANISM: Artificial
<220> FEATURE:
<223> OTHER INFORMATION: Humanized antibody

<400> SEQUENCE: 18
acgcgtccac catgaggacc cctgctcagt tcttggtat cttgttgctc tggtttcctg      60
gtatcaaatg tgacatccag atgacccagt ctccatcttc cctgtctgca tctgttggag    120
acagggtcac tatcacttgc aaagcaagtc aggacattaa tagctattta agctggttcc    180
agcagaaacc agggaaagct cctaagaccc tgatctatcg tgcaaacaga ttggtagatg    240
gggtcccatc aagattcagt ggcagtggat ctgggcaaga ttatactctc accatcagta    300
gcctgcagcc tgaggatttc gcaacttatt attgtctaca gtatgatgag tttccgtaca    360
cgttcggagg agggaccaag gtggaaataa aacgtaagtg cactttcctt ctaga         415

<210> SEQ ID NO 19
<211> LENGTH: 127
<212> TYPE: PRT
<213> ORGANISM: Artificial
<220> FEATURE:
<223> OTHER INFORMATION: Humanized antibody

<400> SEQUENCE: 19

Met Arg Thr Pro Ala Gln Phe Leu Gly Ile Leu Leu Leu Trp Phe Pro
1               5                   10                  15

Gly Ile Lys Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Ile Asn Ser Tyr Leu Ser Trp Phe Gln Gln Lys Pro Gly Lys Ala Pro

```
            50                  55                  60
Lys Thr Leu Ile Tyr Arg Ala Asn Arg Leu Val Asp Gly Val Pro Ser
 65                  70                  75                  80

Arg Phe Ser Gly Ser Gly Ser Gly Gln Asp Tyr Thr Leu Thr Ile Ser
                 85                  90                  95

Ser Leu Gln Pro Glu Asp Phe Ala Thr Tyr Tyr Cys Leu Gln Tyr Asp
            100                 105                 110

Glu Phe Pro Tyr Thr Phe Gly Gly Gly Thr Lys Val Glu Ile Lys
            115                 120                 125

<210> SEQ ID NO 20
<211> LENGTH: 75
<212> TYPE: DNA
<213> ORGANISM: Artificial
<220> FEATURE:
<223> OTHER INFORMATION: Oligonucleotide

<400> SEQUENCE: 20
ctagccacgc gtccaccatg aatggagat ggatctttct cttcctcctg tcaggaacta      60
caggtgtcca ctctg                                                     75

<210> SEQ ID NO 21
<211> LENGTH: 77
<212> TYPE: DNA
<213> ORGANISM: Artificial
<220> FEATURE:
<223> OTHER INFORMATION: Oligonucleotide

<400> SEQUENCE: 21
ttcacagaag ccccaggctt cttcacctca gctccagact gcaccagctg gacctcagag     60
tggacacctg tagttcc                                                   77

<210> SEQ ID NO 22
<211> LENGTH: 75
<212> TYPE: DNA
<213> ORGANISM: Artificial
<220> FEATURE:
<223> OTHER INFORMATION: Oligonucleotide

<400> SEQUENCE: 22
aagcctgggg cttctgtgaa aatatcctgc aaggtttctg gttatgcatt cactaactac     60
aacatgtatt gggtg                                                     75

<210> SEQ ID NO 23
<211> LENGTH: 79
<212> TYPE: DNA
<213> ORGANISM: Artificial
<220> FEATURE:
<223> OTHER INFORMATION: Oligonucleotide

<400> SEQUENCE: 23
ccatagtaag gatcaatata tccaatccac tcaaggccct ttccaggggc ctgcctcacc     60
caatacatgt tgtagttag                                                 79

<210> SEQ ID NO 24
<211> LENGTH: 68
<212> TYPE: DNA
<213> ORGANISM: Artificial
<220> FEATURE:
<223> OTHER INFORMATION: Oligonucleotide

<400> SEQUENCE: 24
```
ggatatattg atccttacta tggtgatcct ggctacagcc agaagttcaa gggcaaggcc    60
acattgac                                                            68

<210> SEQ ID NO 25
<211> LENGTH: 80
<212> TYPE: DNA
<213> ORGANISM: Artificial
<220> FEATURE:
<223> OTHER INFORMATION: Oligonucleotide

<400> SEQUENCE: 25
tgtcctcaga cctcaggctg ctgagctcca tgtaggctgt gctggtggac ttgtcaacag    60
tcaatgtggc cttgcccttg                                               80

<210> SEQ ID NO 26
<211> LENGTH: 79
<212> TYPE: DNA
<213> ORGANISM: Artificial
<220> FEATURE:
<223> OTHER INFORMATION: Oligonucleotide

<400> SEQUENCE: 26
gcagcctgag gtctgaggac actgcagtct attactgtgc aagacgtggc aacttcccgt    60
actactttga ctactgggg                                                79

<210> SEQ ID NO 27
<211> LENGTH: 79
<212> TYPE: DNA
<213> ORGANISM: Artificial
<220> FEATURE:
<223> OTHER INFORMATION: Oligonucleotide

<400> SEQUENCE: 27
gactcgtcta gaggttgtga ggactcacct gatgagactg tgacaagggt gccttggccc    60
cagtagtcaa agtagtacg                                                79

<210> SEQ ID NO 28
<211> LENGTH: 20
<212> TYPE: DNA
<213> ORGANISM: Artificial
<220> FEATURE:
<223> OTHER INFORMATION: Oligonucleotide

<400> SEQUENCE: 28
ctagccacgc gtccaccatg                                               20

<210> SEQ ID NO 29
<211> LENGTH: 21
<212> TYPE: DNA
<213> ORGANISM: Artificial
<220> FEATURE:
<223> OTHER INFORMATION: Oligonucleotide

<400> SEQUENCE: 29
gactcgtcta gaggttgtga g                                             21

<210> SEQ ID NO 30
<211> LENGTH: 71
<212> TYPE: DNA
<213> ORGANISM: Artificial
<220> FEATURE:
<223> OTHER INFORMATION: Oligonucleotide

```
<400> SEQUENCE: 30
ctagccacgc gtccaccatg aggaccnctg ctcagtttct tggtatcttg ttgctctggt    60
ttcctggtat c                                                        71

<210> SEQ ID NO 31
<211> LENGTH: 74
<212> TYPE: DNA
<213> ORGANISM: Artificial
<220> FEATURE:
<223> OTHER INFORMATION: Oligonucleotide

<400> SEQUENCE: 31
caacagatgc agacagggaa gatggagact gggtcatctg gatgtcacat ttgataccag    60
gaaaccagag caac                                                     74

<210> SEQ ID NO 32
<211> LENGTH: 68
<212> TYPE: DNA
<213> ORGANISM: Artificial
<220> FEATURE:
<223> OTHER INFORMATION: Oligonucleotide

<400> SEQUENCE: 32
cttccctgtc tgcatctgtt ggagacaggg tcactatcac ttgcaaagca agtcaggaca    60
ttaatagc                                                            68

<210> SEQ ID NO 33
<211> LENGTH: 72
<212> TYPE: DNA
<213> ORGANISM: Artificial
<220> FEATURE:
<223> OTHER INFORMATION: Oligonucleotide

<400> SEQUENCE: 33
gatcagggtc ttaggagctt tccctggttt ctgctggaac cagcttaaat agctattaat    60
gtcctgactt gc                                                       72

<210> SEQ ID NO 34
<211> LENGTH: 78
<212> TYPE: DNA
<213> ORGANISM: Artificial
<220> FEATURE:
<223> OTHER INFORMATION: Oligonucleotide

<400> SEQUENCE: 34
gaaagctcct aagaccctga tctatcgtgc aaacagattg gtagatgggg tcccatcaag    60
attcagtggc agtggatc                                                 78

<210> SEQ ID NO 35
<211> LENGTH: 66
<212> TYPE: DNA
<213> ORGANISM: Artificial
<220> FEATURE:
<223> OTHER INFORMATION: Oligonucleotide

<400> SEQUENCE: 35
cctcaggctg caggctactg atggtgagag tataatcttg cccagatcca ctgccactga    60
atcttg                                                              66

<210> SEQ ID NO 36
<211> LENGTH: 75
```

-continued

```
<212> TYPE: DNA
<213> ORGANISM: Artificial
<220> FEATURE:
<223> OTHER INFORMATION: Oligonucleotide

<400> SEQUENCE: 36
cagtagcctg cagcctgagg atttcgcaac ttattattgt ctacagtatg atgagtttcc     60
gtacacgttc ggagg                                                     75

<210> SEQ ID NO 37
<211> LENGTH: 72
<212> TYPE: DNA
<213> ORGANISM: Artificial
<220> FEATURE:
<223> OTHER INFORMATION: Oligonucleotide

<400> SEQUENCE: 37
gactcgtcta gaaggaaagt gcacttacgt tttatttcca ccttggtccc tcctccgaac     60
gtgtacggaa ac                                                        72

<210> SEQ ID NO 38
<211> LENGTH: 20
<212> TYPE: DNA
<213> ORGANISM: Artificial
<220> FEATURE:
<223> OTHER INFORMATION: Oligonucleotide

<400> SEQUENCE: 38
ctagccacgc gtccaccatg                                                20

<210> SEQ ID NO 39
<211> LENGTH: 19
<212> TYPE: DNA
<213> ORGANISM: Artificial
<220> FEATURE:
<223> OTHER INFORMATION: Oligonucleotide

<400> SEQUENCE: 39
gactcgtcta gaaggaaag                                                 19
```